(12) United States Patent
Sutoo et al.

(10) Patent No.: US 10,444,152 B2
(45) Date of Patent: Oct. 15, 2019

(54) TISSUE SAMPLE ANALYSIS DEVICE AND TISSUE SAMPLE ANALYSIS SYSTEM

(71) Applicant: YAMATO SCIENTIFIC CO., LTD., Tokyo (JP)

(72) Inventors: Den'etsu Sutoo, Tokyo (JP); Shintaroh Ueda, Toyko (JP); Kayo Akiyama, Tokyo (JP)

(73) Assignee: YAMATO SCIENTIFIC CO., LTD., Tokyo (JP)

( * ) Notice: Subject to any disclaimer, the term of this patent is extended or adjusted under 35 U.S.C. 154(b) by 40 days.

(21) Appl. No.: 15/743,085

(22) PCT Filed: Jul. 6, 2016

(86) PCT No.: PCT/JP2016/070019
§ 371 (c)(1),
(2) Date: Jan. 9, 2018

(87) PCT Pub. No.: WO2017/010375
PCT Pub. Date: Jan. 19, 2017

(65) Prior Publication Data
US 2019/0079012 A1    Mar. 14, 2019

(30) Foreign Application Priority Data
Jul. 10, 2015  (JP) ................. 2015-138702

(51) Int. Cl.
*G06K 9/00*     (2006.01)
*G01N 21/64*    (2006.01)
(Continued)

(52) U.S. Cl.
CPC ..... *G01N 21/6458* (2013.01); *G01N 21/6456* (2013.01); *G06K 9/00127* (2013.01);
(Continued)

(58) Field of Classification Search
CPC ....... G01N 2021/7786; G01N 21/6456; G01N 21/6458; G06K 9/00127; G06T 2207/30024; G06T 7/0014
See application file for complete search history.

(56) References Cited

U.S. PATENT DOCUMENTS

| 5,307,161 A | 4/1994 | Miyamoto |
| 2015/0069268 A1 | 3/2015 | Schoenborn |

FOREIGN PATENT DOCUMENTS

| CA | 2 362 939 A1 | 8/2000 |
| JP | 4-316478 A | 11/1992 |

(Continued)

OTHER PUBLICATIONS

International Search Report for PCT/JP2016/070019, dated Sep. 27, 2016.
(Continued)

*Primary Examiner* — Xin Jia
(74) *Attorney, Agent, or Firm* — Sughrue Mion, PLLC

(57) ABSTRACT

A tissue sample analysis device 1 that quantitatively analyzes photometric information obtained by applying light to a tissue sample M of a living body, the tissue sample analysis device including: a light source unit 30 that applies the light to the tissue sample M; and a flat light receiving unit 31 that is disposed opposite to the light source unit 30, and in a state in which the tissue sample M is disposed between the light source unit 30 and the light receiving unit 31 itself, receives light transmitted through the tissue sample M or light radiated from the tissue sample M.

14 Claims, 12 Drawing Sheets

(51) Int. Cl.
*G06T 7/00* (2017.01)
*G01N 21/77* (2006.01)

(52) U.S. Cl.
CPC .... *G06T 7/0014* (2013.01); *G01N 2021/7786* (2013.01); *G06T 2207/30024* (2013.01)

(56) References Cited

FOREIGN PATENT DOCUMENTS

| | | | |
|---|---|---|---|
| JP | 2002-525587 | A | 8/2002 |
| JP | 2005-227155 | A | 8/2005 |
| JP | 4405837 | A | 1/2010 |
| JP | 2010-276866 | A | 12/2010 |
| JP | 2015-84059 | A | 4/2015 |
| WO | 00/12123 | A2 | 3/2000 |

OTHER PUBLICATIONS

International Preliminary on Patentability Report dated Jan. 11, 2018, issued by the International Searching Authority in application No. PCT/JP2016/070019.

TISSUE SAMPLE ANALYSIS DEVICE AND TISSUE SAMPLE ANALYSIS SYSTEM

CROSS REFERENCE TO RELATED APPLICATIONS

This application is a National Stage of International Application No. PCT/JP2016/070019 filed Jul. 6, 2016, claiming priority based on Japanese Patent Application No. 2015-138702 filed Jul. 10, 2015, the contents of all of which are incorporated herein by reference in their entirety.

TECHNICAL FIELD

The present invention relates to a tissue sample analysis device that in a cellular level, quantifies and images a tissue sample, for example, such as neurotransmitters and neuromodulators in the brain of a living body, and relates to a tissue sample analysis system including the tissue sample analysis device.

BACKGROUND ART

For example, several tens of millions of neurons are distributed in a brain of a human that is a living body, and as results of chemical reactions which occur in the respective cells, every emotion including joy, anger, grief and pleasure and every action are dominated. It is a central theme of the brain research to examine, in the cellular level, what kind of chemical reactions occur in which region of the brain.

The chemical reactions in the brain cells are examined in such a manner that, in order to see the chemical reactions concerned, a test reagent is dropped onto a tissue sample, for example, sliced brain tissues of an animal or the like, and is caused to react with the tissue sample, and a state of a relevant reaction portion is seen.

At a first measurement in measuring work for this reaction portion, the sliced brain tissues are placed on a stage, and a region of the brain cells is measured one point by one point while moving the stage without using the test reagent for the brain cells. When the measurement is completed, this stage is returned to an original position thereof.

Next, at a second measurement, while moving the stage one more time with use of the test reagent for the brain cells, the same spot in the reaction region of the brain cells, which is measured at the first measurement, is measured one point by one point. In this way, measured values on the spot of such a brain cell region without using the test reagent and measured values on the spot of the brain cell region with use of the test reagent are compared with each other for examination.

Patent Literature 1 discloses a tissue sample analysis device that performs such measurement.

In the tissue sample analysis device of Patent Literature 1, a photomultiplier is mounted on a camera mount of a large microscope, and a fluorescence emitted from a region of a very small point (for example, with a diameter of several tens of micrometers) of a tissue sample is focused by a pinhole, and is measured in a photometric manner by using a camera of the large microscope and the photomultiplier.

Next, photometric values of all the regions of the tissue sample are collected while moving the stage, and the obtained photometric value data is constructed on a coordinate, whereby the tissue sample analysis device creates a quantitative distribution map of a substance.

In this tissue sample analysis device, when the first measurement is completed and the second measurement is started, the stage is returned to such an original point. When a position display control unit of the tissue sample analysis device compares position information on a first set position of the stage and a position information on a second set position of the stage with each other, and determines that there is no difference between the position information on the first set position of the stage and the position information on the second set position of the stage, then the position display control unit regards such second stage-set position information as such first stage-set position information, and holds the position information on the first set position of the stage as it is.

Meanwhile, when the position display control unit of the tissue sample analysis device determines that there is a difference between the position information on the first set position of the stage and the position information on the second set position of the stage, then the position display control unit allows screen display of the position information about the first set position of the stage.

CITATION LIST

Patent Document

Patent Literature 1: Japanese Patent No. 4405837

SUMMARY OF THE INVENTION

Problems to be Solved by the Invention

The tissue sample analysis device described in Patent Literature 1 is excellent in analytical sensitivity, quantitativeness and reproducibility, and in accordance with this tissue sample analysis device, the measuring work can be started promptly without being influenced by positional accuracy of the tissue sample when the tissue sample is set on the stage. Therefore, the tissue sample analysis device described in Patent Literature 1 is excellent in that the test reagent localized in the tissue sample can be quantified in a minute range of the tissue sample while maintaining a tissue structure of a macroscopic specimen of the tissue sample.

However, the tissue sample analysis device described in Patent Literature 1 has such problems that a system thereof is large-scale and cost thereof is high, that an analysis operation by an operator is complicated to result in poor operability, that an analysis time for the tissue sample is long, and moreover, that a resolution thereof is not sufficient. If the analysis time for the tissue sample is long, then it is apprehended that the tissue sample may be deteriorated, and accordingly, it is not desirable that the analysis time be long. Moreover, with the rapid advancement of academia, when the tissue sample is analyzed, it is required to obtain finer analysis results and to enable more rapid analysis work.

The present invention has been made in view of the above-described circumstances, and it is an object of the present invention to provide a tissue sample analysis device, which can achieve cost reduction and downsizing, and is capable of accelerating the analysis work for the tissue sample, and to provide a tissue sample analysis system including this tissue sample analysis device.

Solution to Problem

In order to achieve the foregoing object, a tissue sample analysis device according to a first aspect of the present invention is a tissue sample analysis device that quantitatively analyzes photometric information obtained by applying light to a tissue sample of a living body, the tissue sample analysis device including: a light source unit that applies the light to the tissue sample; and a flat light receiving unit that is disposed opposite to the light source unit, and in a state in which the tissue sample is disposed between the light source unit and the light receiving unit itself, receives light transmitted through the tissue sample or light radiated from the tissue sample.

In the tissue sample analysis device according to the first aspect of the present invention, the tissue sample is disposed between the light source unit and the light receiving unit, and accordingly, a distribution of a chemical substance in the entire tissue sample can be acquired as the photometric information at one time in a short time. Moreover, since the photometric information can be acquired at one time in a short as described above, a deterioration of the tissue sample due to aging can be prevented, and variations in technique of the operator of the experiment do not occur. Moreover, when the tissue sample is brought into close contact with the light source unit and the light receiving unit by being sandwiched therebetween, the tissue sample can be measured in a photometric manner while being flattened even if flatness of the tissue sample is poor. From these facts, in accordance with the tissue sample analysis device according to the first aspect of the present invention, the tissue sample analysis device can be reduced in cost and downsized, it is possible to accelerate the analysis work for the tissue sample, and in addition, it becomes possible to quantify and image the chemical substance unevenly distributed in the tissue sample.

A tissue sample analysis device according to a second aspect of the present invention is characterized in that the light applied to the tissue sample by the light source unit is parallel light.

In accordance with the tissue sample analysis device according to the second aspect of the present invention, it is easy to obtain two-dimensionally quantified image with high quantitativeness.

A tissue sample analysis device according to a third aspect of the present invention is characterized in that the light source unit is flat.

In accordance with the tissue sample analysis device according to the third aspect of the present invention, since the light source unit is flat, the light to be applied therefrom becomes likely to be parallel light or light having parallelism similar to the parallel light. Accordingly, it is easy to obtain such a two-dimensionally quantified image with high quantitativeness. Moreover, when the tissue sample is brought into close contact with the light source unit and the light receiving unit by being sandwiched therebetween, the tissue sample can be expected to be brought into closer contact therebetween by the fact that the light source unit is flat.

A tissue sample analysis device according to a fourth aspect of the present invention is characterized in that the tissue sample is a tissue sample added with a test reagent.

In accordance with the tissue sample analysis device according to the fourth aspect of the present invention, when the chemical substance contained in the tissue sample changes to the photometric information by addition of the test reagent, a distribution of the chemical substance in the entire tissue sample can be acquired.

A tissue sample analysis device according to a fifth aspect of the present invention is characterized in that the test reagent is a fluorescent substance, a band-pass filter that allows transmission of excitation light exciting the fluorescent substance added to the tissue sample is disposed between the light source unit and the tissue sample, and an absorption filter that allows transmission of fluorescence radiated from the fluorescent substance added to the tissue sample is disposed between the tissue sample and the light receiving unit.

In accordance with the tissue sample analysis device according to the fifth aspect of the present invention, the band-pass filter can give the tissue sample only light having a wavelength that fluoresces the fluorescent substance as the test reagent added to the tissue sample. The fluorescence emitted by the fluorescent substance of the tissue sample transmits through the absorption filter, and leakage light of other excitation light and the like are blocked or removed by the absorption filter, and accordingly, the light receiving unit can be surely allowed to receive only the fluorescence or substantially only the fluorescence. Therefore, it becomes possible to quantify and image the chemical substance unevenly distributed in the tissue sample.

A tissue sample analysis device according to a sixth aspect of the present invention is characterized in that the test reagent is stain.

In accordance with the tissue sample analysis device according to the sixth aspect of the present invention, for example, the tissue sample such as lipid, which is unsuitable for the immunohistochemical staining, is dyed with such a general histochemical stain or the like, and accordingly, in a photometric manner, the light receiving unit can measure the distribution of the concentration of the target substance in the tissue sample as a distribution of the transmittance.

A tissue sample analysis device according to a seventh aspect of the present invention is characterized in that a band-pass filter that allows transmission of only a light component in a wavelength region in which the stain added to the tissue sample is largely absorbed is disposed between the light source unit and the tissue sample.

In accordance with the tissue sample analysis device according to the seventh aspect of the present invention, when the tissue sample M stained by the histochemical stain is measured in a photometric manner, absorbance of such a stained portion stained by the histochemical stain can be measured with higher accuracy.

A tissue sample analysis device according to an eighth aspect of the present invention is characterized in that an absorption filter that allows the transmission of only the light component in the wavelength region in which the stain added to the tissue sample is largely absorbed is disposed between the tissue sample and the light receiving unit.

In accordance with the tissue sample analysis device according to the eighth aspect of the present invention, when the tissue sample M stained by the histochemical stain is measured in a photometric manner, the absorbance of the stained portion stained by the histochemical stain can be measured with higher accuracy.

A tissue sample analysis device according to a ninth aspect of the present invention is characterized in that the light receiving unit is composed by two-dimensionally arranging solid-state image sensors.

In accordance with the tissue sample analysis device according to the ninth aspect of the present invention, it is only necessary to two-dimensionally arrange the solid-state image sensors as the light receiving unit, and accordingly, there is no need to use a large microscope or photomultiplier or both of them. Therefore, the tissue sample analysis device can be downsized to a large extent, and cost thereof can be reduced to a large extent.

A tissue sample analysis device according to a tenth aspect of the present invention is characterized in that the light source unit is composed by arranging a plurality of light emitting diodes in two dimensions.

In accordance with the tissue sample analysis device according to the tenth aspect of the present invention, it is only necessary to arrange, as the light source unit, the plurality of light emitting diodes in two dimensions, and accordingly, there is no need to use such a large microscope or photomultiplier or both of them. Therefore, the tissue sample analysis device can be downsized to a large extent, and cost thereof can be reduced to a large extent.

A tissue sample analysis device according to an eleventh aspect of the present invention is characterized in that the light source unit is composed of electroluminescence in a flat plate shape, and the light receiving unit is composed by two-dimensionally arranging solid-state image sensors.

In accordance with the tissue sample analysis device according to the eleventh aspect of the present invention, the light source unit is composed of electroluminescence in the flat plate shape, and it is only necessary to two-dimensionally arrange the solid-state image sensors as the light receiving unit, and accordingly, there is no need to use such a large microscope or photomultiplier or both of them. Therefore, the tissue sample analysis device can be downsized to a large extent, and cost thereof can be reduced to a large extent.

A tissue sample analysis device according to a twelfth aspect of the present invention is characterized in that a protection mechanism that prevents damage due to contact between the light source unit or the light receiving unit and the tissue sample or a preparation containing the tissue sample is provided.

In accordance with the tissue sample analysis device according to the twelfth aspect of the present invention, direct contact between a light source unit 30 or a light receiving unit 31, and a tissue sample M or a preparation containing the tissue sample M, and breakage thereof can be prevented.

A tissue sample analysis system according to a thirteenth aspect of the present invention includes: the tissue sample analysis device; a high-definition image acquisition device that acquires a high-definition image of the tissue sample; and an integration control unit that associates the quantified image created by the tissue sample analysis device and the high-definition image acquired by the high-definition image acquisition device with each other.

In accordance with the tissue sample analysis system according to the thirteenth aspect of the present invention, a quantified image created by the tissue sample analysis device and the high-definition image acquired by the high-definition image acquisition device are associated with each other, and accordingly, it is possible to analyze the chemical substance in the tissue sample by a two-dimensional image composite in which such a quantified image with excellent quantitativeness and the high-definition image with high resolution are linked and associated with each other by coordinates. Moreover, a three-dimensional image composite can also be created, in which two-dimensional image composites of a plurality of consecutive tissue sections are three-dimensionally constructed. For example, it is possible to create and reconstruct the three-dimensional composite by adding a thickness at the time of cutting the consecutive tissue sections to coordinate information.

A tissue sample analysis system according to a fourteenth aspect of the present invention includes: the tissue sample analysis device; a high-definition image reading unit that reads a high-definition image of the tissue sample; and an integration control unit that associates the quantified image created by the tissue sample analysis device and the high-definition image read by the high-definition image reading unit with each other.

In accordance with the tissue sample analysis system according to the fourteenth aspect of the present invention, a quantified image created by the tissue sample analysis device and the high-definition image read by the high-definition image reading unit are associated with each other, and accordingly, it is possible to analyze the chemical substance in the tissue sample by a two-dimensional image composite in which such a quantified image with excellent quantitativeness and the high-definition image with high resolution are linked and associated with each other by coordinates.

Moreover, a three-dimensional image composite can also be created, in which two-dimensional image composites of a plurality of consecutive tissue sections are three-dimensionally constructed. For example, it is possible to create and reconstruct the three-dimensional composite by adding a thickness at the time of cutting the consecutive tissue sections to coordinate information.

Effects of the Invention

In accordance with the tissue sample analysis device according to the present invention, the cost reduction and the downsizing can be achieved, and it is possible to accelerate the analysis work for the tissue sample. In accordance with the tissue sample analysis system of the present invention, in addition to the effect of the tissue sample analysis device according to the present invention, it is possible to analyze the chemical substance in the tissue sample by the two-dimensional and three-dimensional image composites in each of which the quantified image with excellent quantitativeness and the high-definition image with high resolution are linked and associated with each other by the coordinates.

BRIEF DESCRIPTION OF DRAWINGS

FIG. 3 is a perspective view showing a light source unit, a light receiving unit, a tissue sample M, and the like.

FIG. 4 is a front view showing the light source unit, the light receiving unit, the tissue sample M, and the like.

DESCRIPTION OF EMBODIMENTS

First, a description will be made of a tissue sample analysis device with reference to the drawings.

[Tissue Sample Analysis Device]

First Embodiment

Figure 1:
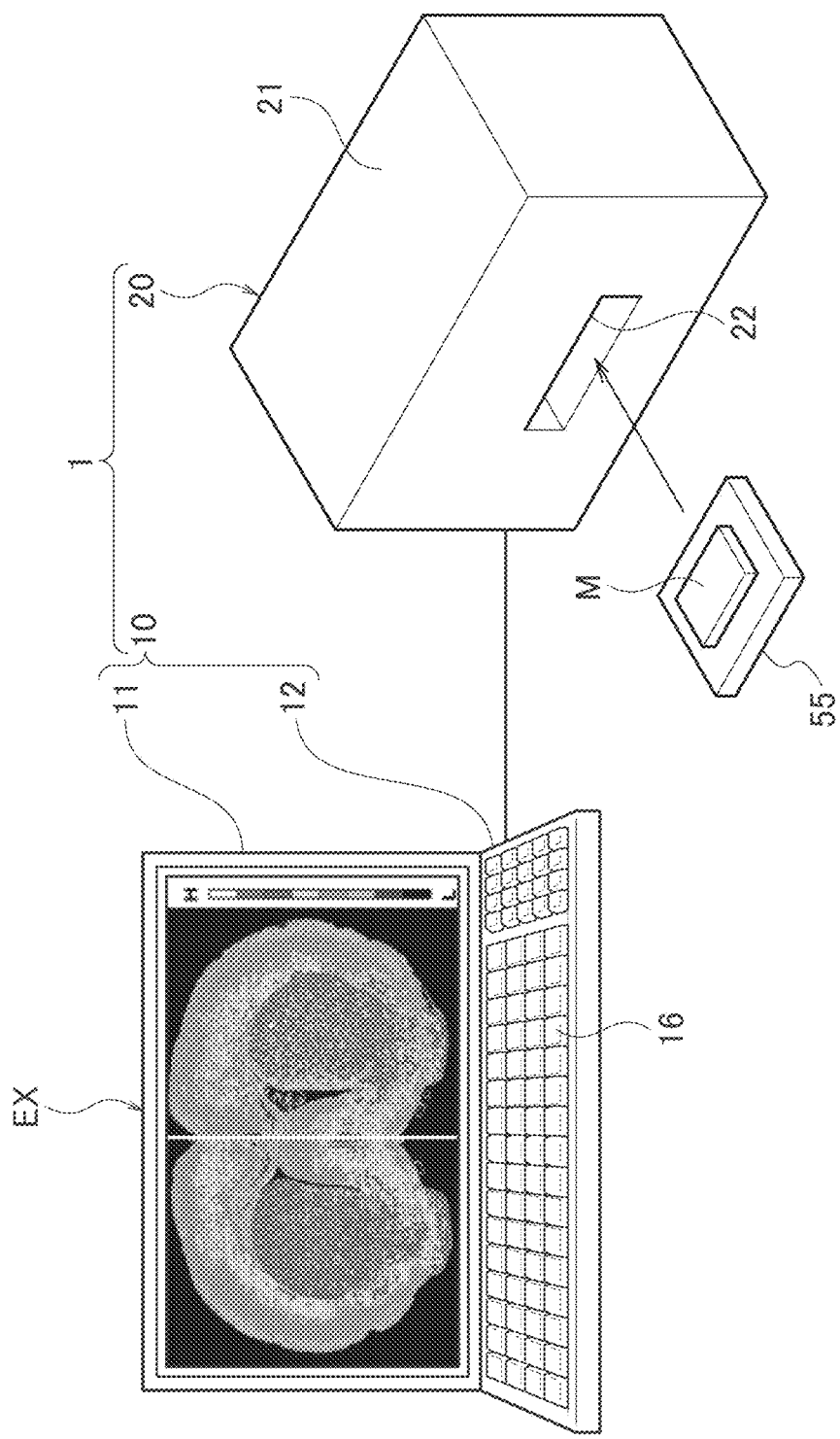
FIG. 1 is an overall view showing a tissue sample analysis device according to a first embodiment of the present invention.
Figure 2:
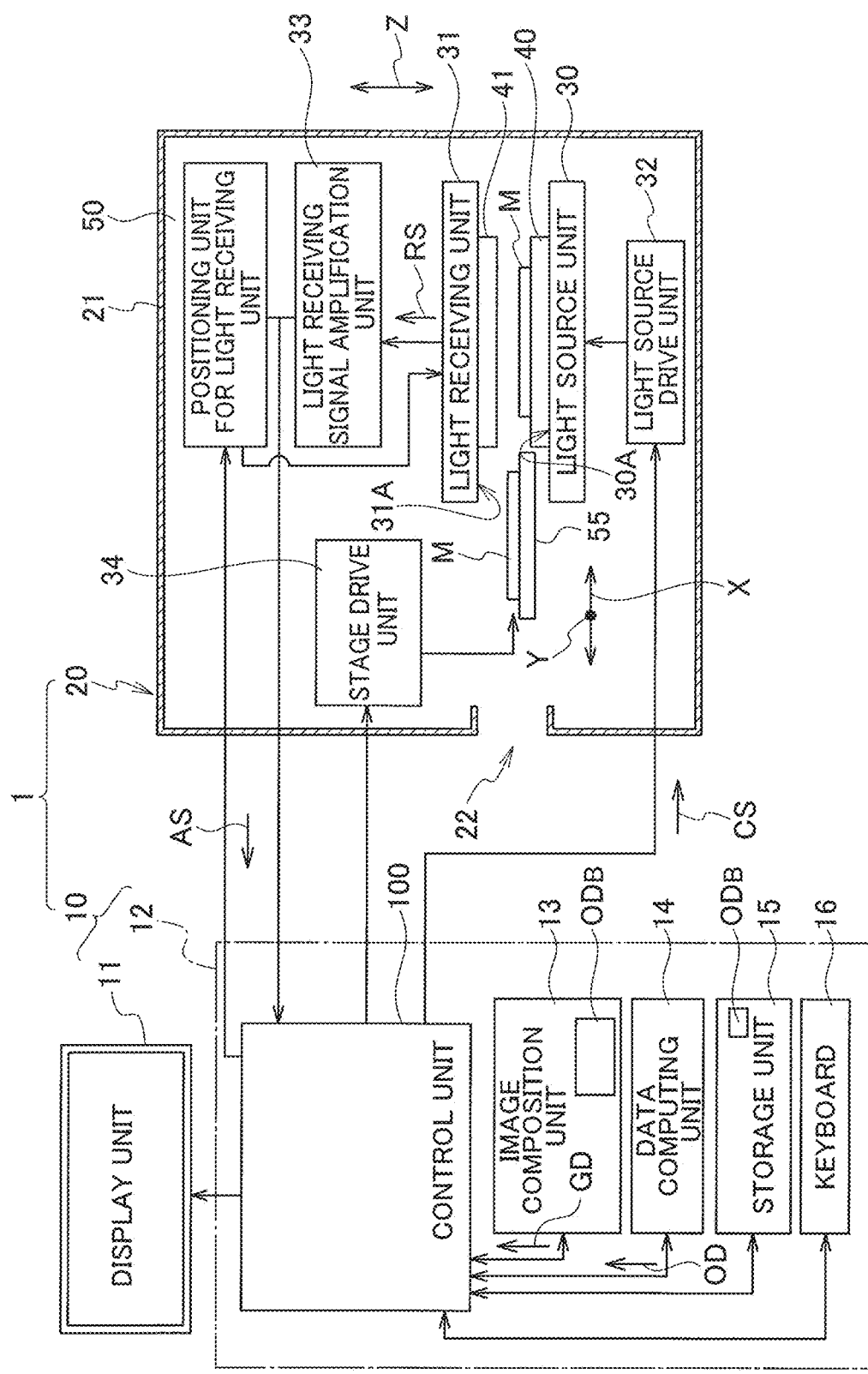
FIG. 2 is a block diagram showing a configuration example of the tissue sample analysis device shown in FIG. 1.

FIG. 1 is an overall view showing a tissue sample analysis device according to a first embodiment of the present invention. FIG. 2 is a block diagram showing a configuration example of the tissue sample analysis device shown in FIG. 1.

A tissue sample analysis device 1 shown in FIG. 1 and FIG. 2 has an ability to analyze photometric information of one tissue sample M of a living body, for example, in a few minutes no matter how large the tissue sample M may be. This tissue sample analysis device 1 can also be referred to as a tissue sample analyzer or a quantitative lensless imaging analyzer. The tissue sample analysis device 1 is necessary for the following purposes.

All life phenomena are dominated by chemical substances in cells distributed in the respective tissues, and it is important to quantify chemical substances in such cells of regions, which are responsible for functions, in order to elucidate the activities of life. Moreover, abnormal changes in chemical reactions in a local region may cause serious diseases, and in order to elucidate mechanisms of pathogenesis of these diseases, it is important to quantify changes in chemical substances in cells in micro regions.

Heretofore, in order to quantify (quantitatively analyze) the changes of the chemical substances in the cells, analysis of biological substances has been carried out by various methods for many years. In 1985, the inventors of the present invention developed and commercialized a mapping analyzer device, which quantifies and images, in a microscopic level, chemical substances distributed in a tissue sample, as a device that quantitatively analyzes such localized chemical substances while maintaining a tissue structure of the tissue sample.

This device, in a photometric manner, finely measures an intensity of a fluorescence emitted from a target substance and an absorption intensity in the tissue sample immunohistochemically stained on a slide glass. By this technique, the above-described device makes it possible to quantitatively image the chemical reactions at the time when a variety of life phenomena emerge. Moreover, the above-described device elucidates the mechanisms of pathogenesis by using model animals of several diseases and pathological tissue samples of human.

At research sites, such a mapping analyzer device as described above is used as a leading-edge measurement/analysis instrument for elucidation of basic mechanisms of the life phenomena, for elucidation of the mechanisms of pathogenesis of diseases, and newly in addition, for development of therapeutic drugs. The mapping analyzer device has received a high evaluation in the domestic and overseas, and is playing a leading role in the development of the microscopic imaging device.

In contrast, a laser confocal microscope, which entered the market late, and a microscopic imaging device, which uses a CCD (Charge-Coupled Device), provide a clear and fine tissue image; however, have a problem in quantitativeness. An imaging mass spectrometer cannot easily distinguish a distribution of biological substances having the same mass.

As described above, there is no other device than the mapping analyzer device, which is excellent in quantifying the chemical substances, which are localized in the tissue sample, in a minute range of the tissue sample while maintaining a tissue structure of a macroscopic specimen. However, the mapping analyzer device has such problems that a scale thereof is large, that an analysis operation is complicated, and that an analysis time is long. Therefore, with the rapid advancement of academia in this field, finer analysis and faster analysis are required.

The tissue sample analysis device 1 according to the first embodiment of the present invention solves such problems as described above, is made capable of achieving cost reduction and downsizing, makes it possible to analyze photometric information in finer regions of the tissue sample M, and makes it possible to accelerate the analysis work for the tissue sample M.

Next, a structure example of the tissue sample analysis device 1 will be described with reference to FIG. 1 and FIG. 2.

As shown in FIG. 1 and FIG. 2, the tissue sample analysis device 1 is a tissue sample analysis device that quantitatively analyzes photometric information obtained by applying light to a tissue sample of a living body. The tissue sample analysis device 1 includes: a light source unit 30 that applies light to the tissue sample; and a flat light receiving unit 31 that is disposed opposite to the light source unit 30, and in a state in which the tissue sample is disposed between the light source unit 30 and the light receiving unit 31 itself, receives light transmitted through the tissue sample or light radiated from the tissue sample.

The tissue sample analysis device 1 is a device, which obtains two-dimensional distribution information (hereinafter, also referred to as "distribution information OD") of photometric information AS of the tissue sample M, and performs quantification and two-dimensional imaging for the tissue sample M. The tissue sample analysis device 1 includes a control device 10 and a tissue sample analysis unit 20.

The tissue sample analysis unit 20 has a function to acquire the photometric information AS from the tissue sample M. The control device 10 has functions to create various pieces of information based on the photometric information AS acquired by the tissue sample analysis unit 20, to control the tissue sample analysis unit 20, and to perform various computational operations. As the control device 10, for example, a compact general-purpose computer (PC) can be used. The compact general-purpose computer is used as described above, whereby the cost reduction and downsizing of the tissue sample analysis device 1 can be achieved.

Here, a description will be made of the photometric information AS, the two-dimensional distribution information (distribution information OD) of the photometric information AS, and the quantification and two-dimensional imaging of the tissue sample M, those of which are described above.

<Photometric Information AS, Photometric Value RS>

The photometric information AS of the tissue sample M is information composed of a numerical sequence in which coordinate information in the light receiving unit 31 is added to the photometric values RS. Here, the photometric value RS is information obtained in such a manner that each of a large number of photoelectric conversion elements which compose the light receiving unit 31 converts light into an electrical signal, the light being illumination light applied from the light source unit 30 and transmitted through the tissue sample M or illumination light radiated from the tissue sample M. As described later, as the photoelectric conversion element, for example, a light receiving element of a complementary metal oxide semiconductor (CMOS) image sensor (solid-state image sensor) is used. The photometric value RS is expressed as a gradation value of light detected by one pixel formed of, for example, a CMOS image sensor element that composes the light receiving unit 31. The photometric value RS is, for example, information corresponding to a quantitative analysis value of a chemical substance unevenly distributed in the tissue sample M.

When the photometric value RS of the tissue sample M is the gradation value of the light sensed by one pixel as described above, then the photometric information AS of the tissue sample M is, for example, information in which coordinate information of the one pixel in the light receiving unit 31 is added to the gradation value of the light sensed by the one pixel of the light receiving unit 31 concerned.

Note that, with regard to the photometric value RS, depending on a condition of the test reagent or the chemical substances, such as a fluorescent substance present in the tissue sample M, a spectrum of the transmitted light of the tissue sample M may change, light of a specific wavelength may be absorbed by the test reagent or chemical substance of the tissue sample M, and an intensity of a specific wavelength of the transmitted light of the tissue sample M may change. Due to such properties as described above, in accordance with the photometric value RS, properties of the chemical substances in the tissue sample M and an amount of the chemical substances therein can be measured. Moreover, in accordance with the photometric value RS, it is possible to measure chemical substances such as pigment, which was originally present in the tissue sample M, even in a state in which no test reagent such as a fluorescent substance is present in the tissue sample M.

<Two-Dimensional Distribution Information (Distribution Information OD) of Photometric Information AS>

The two-dimensional distribution information (distribution information OD) of the photometric information AS of the tissue sample M is information in which a large number of the photometric values RS included in a large number of the photometric information AS are arranged two-dimensionally so as to correspond to coordinate information, in which the respective photometric values RS are present, in the light receiving unit 31. Specifically, the distribution information OD is information composed of a numerical matrix in which the photometric values RS are arranged based on the coordinate information in the light receiving unit 31, which is added to the photometric information AS.

For example, when the photometric value RS of the tissue sample M is the gradation value of the light sensed by one pixel, the distribution information OD is information composed of a numerical matrix of the gradation values of the light, in which the gradation values of a large number of pieces of the light sensed by a large number of pixels are two-dimensionally arranged based on the coordinate information of the respective pixels in the light receiving unit 31. Note that the distribution information OD is information serving as a source from which two-dimensionally imaged data GD, which is information for displaying a two-dimensional image on the display unit 11, is created. The two-dimensional image can be composed by performing computational processing for the distribution information OD.

Here, the distribution information OD of the tissue sample M is considered by using an example where the light receiving unit 31 has a rectangular shape in which quadrangular pixels having sides parallel to each other in vertical and horizontal directions are arranged two-dimensionally by a large number, and where the tissue sample M has a rhombus shape having corner portions directed in the vertical and horizontal directions of the light receiving unit 31. In usual, a size of the pixel of the light receiving unit 31 is not so small as to be able to reproduce shapes of the corner portions and oblique sides of the tissue sample M as they are.

Therefore, in general, the large number of photometric values RS which compose the distribution information OD of the tissue sample M are lower in compliance with the shape of the tissue sample M as compared with a high-definition image taken in a microscope photograph or the like.

<Quantification of Tissue Sample M>

The quantification of the tissue sample M means to associate a quantitative analysis value of an amount of the chemical substance, which is unevenly distributed in the tissue sample M, with each of areas corresponding to the respective photoelectric conversion elements which compose the light receiving unit 31. In this embodiment, the quantification of the tissue sample M is achieved by creating the distribution information OD of the tissue sample M. As mentioned above, the distribution information OD of the tissue sample M is the information composed of the numerical matrix of the gradation values of light, in which the photometric values RS such as the gradation values of the light are two-dimensionally arranged based on the coordinate information of the respective photoelectric conversion elements in the light receiving unit 31. When each of the photometric values RS is set so as to correspond to the quantitative analysis value of the amount of the chemical substance, the quantification of the tissue sample M is achieved by creating the distribution information OD of the tissue sample M.

<Two-Dimensional Imaging of Tissue Sample M>

The two-dimensional imaging of the tissue sample M means to create the two-dimensionally imaged data GD that is image data composing the two-dimensional image from the distribution information OD.

<Control Device>

A description will be made of the control device 10.

As shown in FIG. 1 and FIG. 2, the control device 10 includes the display unit 11, and a control body unit 12. The control body unit 12 includes a control unit 100, an image composition unit 13, a data computing unit 14, a storage unit 15, and a keyboard 16. The display unit 11 is electrically connected to the control unit 100 of the control body unit 12, and is made capable of displaying a two-dimensional image of the tissue sample M and a high-definition image such as a micrograph, which is acquired from outside the tissue sample analysis device 1, based on a control signal from the control unit 100. As the two-dimensional image of the tissue sample M, for example, a two-dimensional image is used, in which the chemical substance contained in the tissue sample M is quantified and displayed. The control signal from the control unit 100 includes, for example, the two-dimensionally imaged data GD and the like, which will be described later. The two-dimensionally imaged data GD is image data, which is subjected to a variety of computational processing by the control device 10 and finally created by the image composition unit 13 based on the photometric information AS acquired from the tissue sample M by the tissue sample analysis unit 20. As the display unit 11, for example, a color liquid crystal display device can be used.

By the control signal from the control unit 100, as shown in FIG. 1, the display unit 11 can perform color display, for example, for an analysis example EX of an effect of music on a brain function. In the analysis example EX shown in FIG. 1, when a rat is allowed to listen to music (in a right figure), a concentration of a neurotransmitter that obtains pleasure (that is, dopamine) is more significantly increased than when the rat is not allowed to listen to music (in a left figure). The analysis example EX is an example where changes in emotion are two-dimensionally imaged in a molecular manner.

As shown in FIG. 2, the control unit 100 of the control body unit 12 is electrically connected to the image composition unit 13, the data computing unit 14, the storage unit 15 and the keyboard 16 as an information input unit. In this way, the control unit 100 is made capable of exchanging information with the image composition unit 13, the data computing unit 14, the storage unit 15 and the keyboard 16.

The data computing unit 14 has a function to perform the computational processing based on the photometric information AS, which is obtained from the tissue sample analysis unit 20 by analyzing the tissue sample M, and to create the two-dimensional distribution information (distribution information OD) of the photometric information AS. As described above, the distribution information OD is such information serving as a source from which the two-dimensionally imaged data GD, which is image data for displaying a two-dimensional image on the display unit 11, is to be created. When the distribution information OD is computationally processed by the image composition unit 13 described below, the two-dimensionally imaged data GD, which is image data for displaying the two-dimensional image on the display unit 11, is composed.

The image composition unit 13 has a function to compose the two-dimensionally imaged data GD from the distribution information OD. Here, the two-dimensionally imaged data GD is image data for displaying the two-dimensional image on the display unit 11. The storage unit 15 stores information such as the distribution information OD and the two-dimensionally imaged data GD. By using the keyboard 16, a user of the tissue sample analysis device 1 can input necessary data and information to the control unit 100, and can input instructions to the control unit 100.

<Tissue Sample Analysis Unit>

Next, a description will be made of the tissue sample analysis unit 20.

As shown in FIG. 1 and FIG. 2, the tissue sample analysis unit 20 includes a box-shaped housing 21, and an opening portion 22 for putting the tissue sample M is provided on a front side of the housing 21. The tissue sample analysis unit 20 has a function to analyze the chemical substance localized in the tissue sample M and quantify the chemical substance in a minute range of the tissue sample M in such a manner that the test reagent such as the fluorescent substance is added to the tissue sample M, and that the light receiving unit 31 receives light such as a fluorescence emitted by the test reagent based on the light applied from the light source unit 30, and performs photoelectric conversion for the received light.

Note that a following operation mode is referred to as a fluorescence mode, in which a fluorescent substance is used as the test reagent, the fluorescent substance is added to the tissue sample M, and the light receiving unit 31 receives a fluorescence emitted by this fluorescent substance, whereby the chemical substance localized in the tissue sample M is analyzed, and is quantified in the minute range of the tissue sample M.

As shown in FIG. 2, in an inside of the housing 21, there are housed the light source unit 30, the light receiving unit 31, a light source drive unit 32, a light receiving signal amplification unit 33, and a stage drive unit 34.

The light source unit 30 is composed, for example, by arranging a plurality of light emitting diodes in two dimensions. Note that, as will be described later, the light source unit 30 may be composed in a flat shape by electroluminescence, for example. When the light source unit 30 is flat, then as will be described later, the tissue sample M can be sandwiched and held between the light receiving unit 31 and the light source unit 30 concerned, and a measured surface of the tissue sample M can be flattened. Note that, in the case of using such a tissue sample M in which the measured surface is flat, it becomes unnecessary to flatten the measured surface of the tissue sample M by sandwiching the tissue sample M between the light source unit 30 and the light receiving unit 31. Therefore, the light source unit 30 is also configurable so as not to be flat. The light receiving unit 31 is composed by, for example, two-dimensionally arranging solid-state image sensors. Note that, as will be described later, the light receiving unit 31 may be composed by, for example, two-dimensionally arranging solid-state image sensors.

As shown in FIG. 2, the light source unit 30 and the light receiving unit 31 are disposed opposite and parallel to each other so that the tissue sample M can be disposed therebetween, and preferably, sandwiched and held therebetween. The light source unit 30 and the light receiving unit 31 have substantially the same size, and both have a rectangular shape or a square shape. Note that the shape of the light source unit 30 and the light receiving unit 31 is not limited to the rectangular shape or the square shape as long as the light source unit 30 and the light receiving unit 31 can sandwich and hold the tissue sample M. The light source unit 30 is disposed on a lower side of the figure, and the light receiving unit 31 is disposed on an upper side of the figure.

The light source unit 30 shown in FIG. 2 is a plate-shaped light emitting body disposed along an X-direction and a Y-direction perpendicular to the X-direction. As such a light source unit 30 as described above, for example, a self-luminous panel-type light source unit 30 is used, in which a plurality of LEDs (light emitting diodes) are two-dimensionally arranged along the X-direction and the Y-direction.

The light source unit 30 is electrically connected to the light source drive unit 32. The light source drive unit 32 is electrically connected to the control unit 100, and upon acquiring a light source control signal CS from the control unit 100, drives the light source unit 30, and causes the light source unit 30 to emit light all at once.

The light receiving unit 31 is flat, is disposed opposite to the light source unit 30, and receives the light, which is transmitted through the tissue sample M, or the light, which is radiated from the tissue sample M, in a state of disposing the tissue sample M between the light source unit 30 and the light receiving unit 31 concerned, and preferably, in a state of sandwiching the tissue sample M between the light source unit 30 and the light receiving unit 31 concerned. The light receiving unit 31 includes the photoelectric conversion elements, and has a function to receive the light such as the fluorescence, which is emitted by the test reagent in the tissue sample M based on the light applied from the light source unit 30, to perform the photoelectric conversion for the received light, and to create the photometric information AS. For example, the light receiving unit 31 is composed, for example, so that a plurality of light receiving elements of a CMOS (Complementary Metal Oxide Semiconductor) image sensor (solid-state image sensors) as the photoelectric conversion element can be arranged on a plane. An example of the light receiving unit 31 can include a unit in which light receiving elements of a plurality of the CMOS image sensors (solid-state image sensors) are two-dimensionally arranged along the X-direction and the Y-direction. The CMOS image sensor elements for use in the light receiving unit 31 are arranged one by one in sections, for example, partitioned in a matrix grid pattern at a pitch of several microns. One section of the CMOS image sensor elements correspond to one pixel.

The light receiving signal amplification unit 33 is electrically connected to the light receiving unit 31. The light receiving signal amplification unit 33 has a function to amplify the photometric value RS included in the photometric information AS acquired from the light receiving unit 31. Moreover, the light receiving signal amplification unit 33 is electrically connected to the control unit 100 of the control body unit 12. In this way, the light receiving signal amplification unit 33 can send the photometric information AS, which has the amplified photometric value RS, to the control unit 100.

Figure 3:
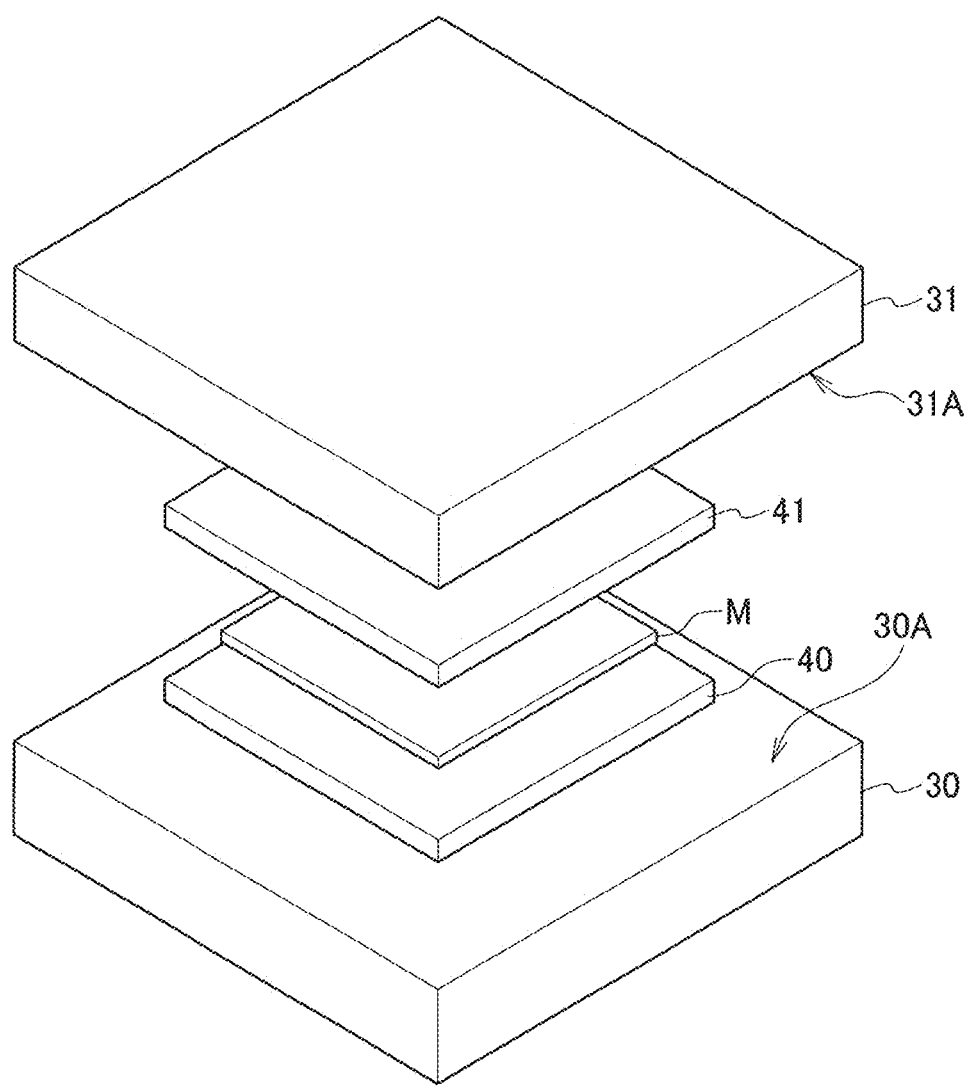
Figure 4:
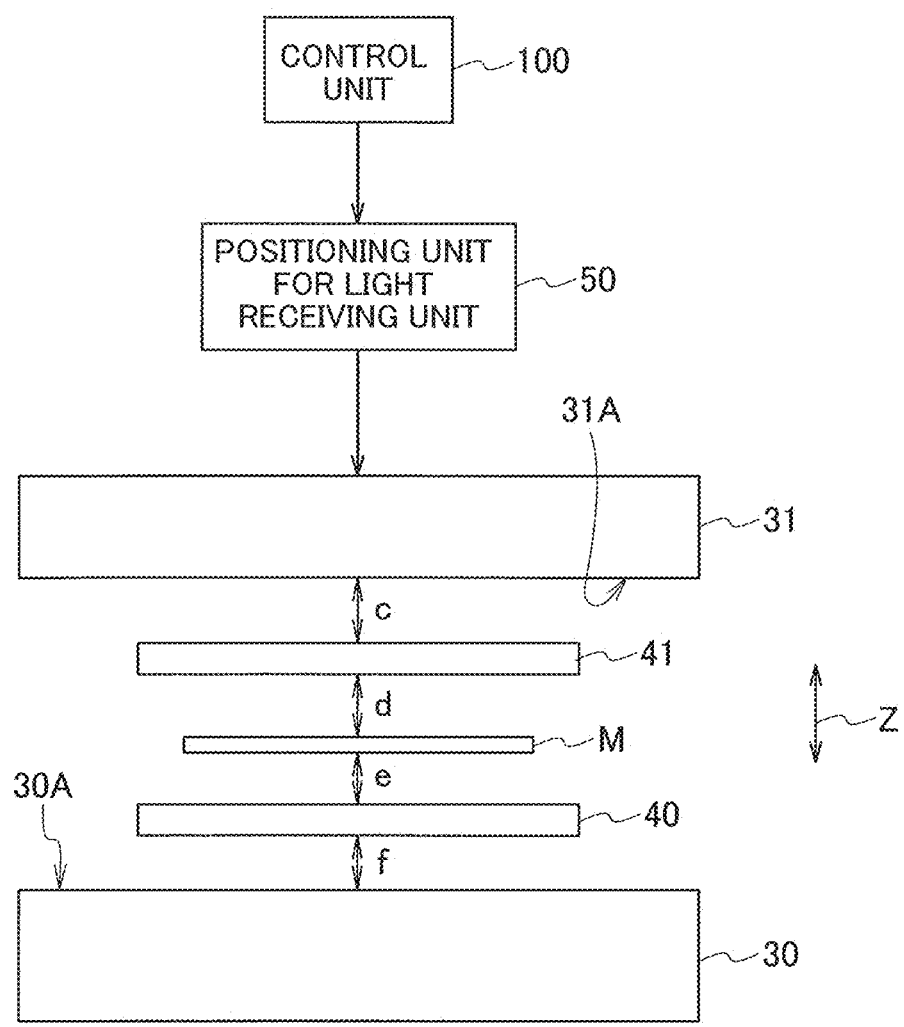
Figure 5:
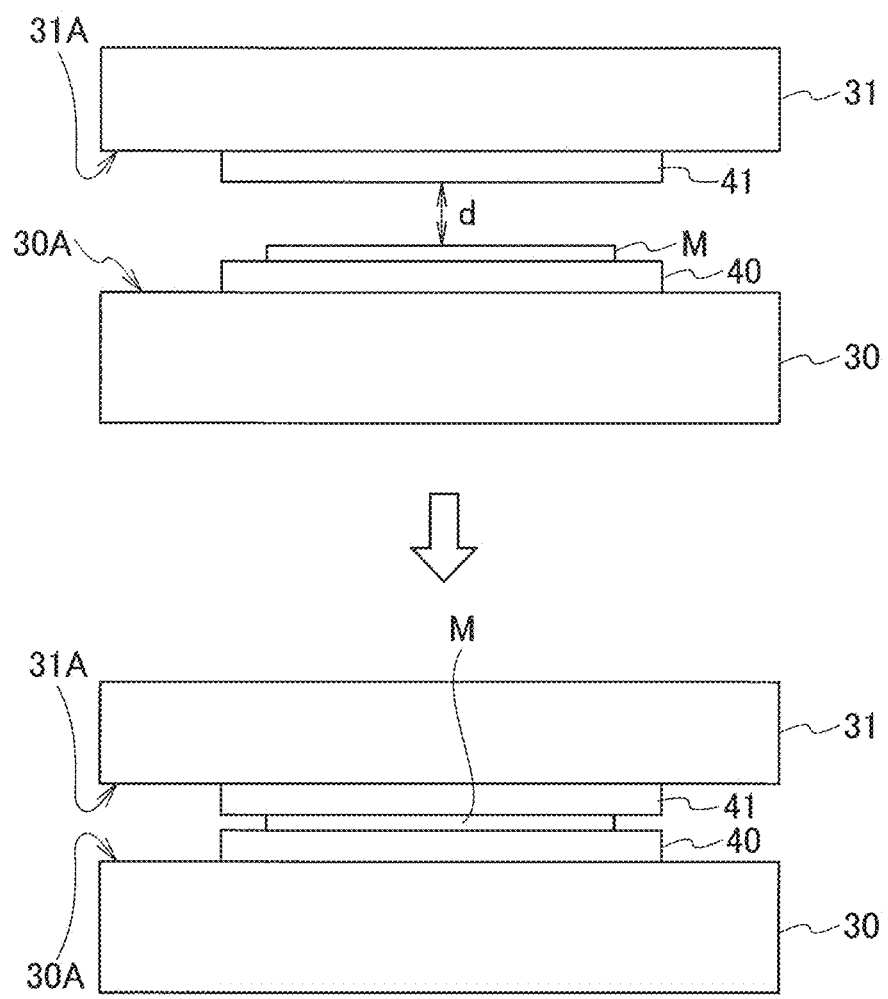
FIG. 5 is a view showing an interval d between an upper surface of the tissue sample M and a lower surface of an absorption filter.

A description will be made of the light source unit 30 and the light receiving unit 31 with reference to FIG. 3 and FIG. 4. FIG. 3 is a perspective view showing the light source unit 30, the light receiving unit 31, the tissue sample M and the like, and FIG. 4 is a front view showing the light source unit 30, the light receiving unit 31, the tissue sample M and the like. FIG. 5 is a view showing an interval d between an upper surface of the tissue sample M and a lower surface of an absorption filter 41.

As shown in FIG. 3 and FIG. 4, a band-pass filter 40 and the absorption filter 41 are disposed between the light source unit 30 and the light receiving unit 31. The band-pass filter 40 is a filer having properties of allowing transmission of primary light such as excitation light applied from the light source unit 30 that excites the fluorescent substance added to the tissue sample, and meanwhile, of not allowing transmission of light other than the primary light. Moreover, the absorption filter 41 is a filter having properties of not transmitting therethrough or removing the above-described primary light, and meanwhile, receiving the primary light, transmitting therethrough the fluorescence radiated by the fluorescent substance added to the tissue sample, and guiding the transmitted fluorescence to a lower surface (light receiving surface) 31A side of the light receiving unit 31.

FIG. 3 and FIG. 4 show an example where the band-pass filter 40 and the absorption filter 41 are formed in a shape similar to that of the light source unit 30 and the light receiving unit 31, and are formed in a size equal to or a little smaller than that of the light source unit 30 and the light receiving unit 31. Specifically, each of the light source unit 30 and the light receiving unit 31 is a rectangular or square plate-shaped member. Moreover, in terms of size, the band-pass filter 40 and the absorption filter 41 are formed a little smaller than the light source unit 30 and the light receiving unit 31.

Note that, in the present invention, a relationship between the sizes of the light source unit 30, the light receiving unit 31, the band-pass filter 40 and the absorption filter 41 is not particularly limited. For example, in terms of size, each of the band-pass filter 40 and the absorption filter 41 may be formed larger than the light source unit 30 and the light receiving unit 31. For example, in terms of size, the band-pass filter 40 and the absorption filter 41 can be formed equal to or larger than the light source unit 30 and the light receiving unit 31, and the light source unit 30 and the light receiving unit 31 can be formed larger than the tissue sample M.

The tissue sample M of the living body, which is shown in FIG. 4 and FIG. 5, is a sample in which it is made possible to quantify the chemical substance, which is localized in the tissue sample M, in the minute range of the tissue sample M by analyzing the chemical substance concerned. The tissue sample M is a sample composed of a tissue sample labeled by the test reagent such as the fluorescent substance, or of a tissue sample itself that is not labeled by the test reagent or the like. That is, the tissue sample M may be a tissue sample to which the test reagent is added, or a tissue sample to which the test reagent is not added. As the test reagent to be added to the tissue sample M, a fluorescent substance or a stain can be used. As the fluorescent substance, coloring matter such as a commercially available fluorescent labeling reagent, for example, a rhodamine derivative or the like can be used.

The tissue sample analysis device 1 is a device to be used for adding the fluorescent substance to the tissue sample M, and is configured to be suitable for adding the fluorescent substance to the tissue sample M. That is, in the tissue sample analysis device 1, the tissue sample M is disposed between the band-pass filter 40 and the absorption filter 41 as shown in FIG. 2 to FIG. 4. In terms of size, the tissue sample M is formed a little smaller than the band-pass filter 40 and the absorption filter 41.

In the example shown in FIG. 3 and FIG. 4, preferably, the size of the band-pass filter 40 and the absorption filter 41 is set a little smaller than the size of the light source unit 30 and the light receiving unit 31. Moreover, the size of the tissue sample M is set a little smaller than the size of the band-pass filter 40 and the absorption filter 41. When the sizes of the band-pass filter 40, the absorption filter 41, the light source unit 30, the light receiving unit 31 and the tissue sample M satisfy such relationships as described above, then the analysis of the chemical substance localized in the entire region of the tissue sample M can be reliably quantified in the minute range of the tissue sample M.

Here, examples of interval values between the respective elements shown in FIG. 4 will be described.

As shown in FIG. 4, an interval between a light emitting surface 30A of the light source unit 30 and a lower surface of the band-pass filter 40 is denoted by reference symbol f, and an interval between an upper surface of the band-pass filter 40 and a lower surface of the tissue sample M is denoted by reference symbol e. Moreover, an interval between the upper face of the tissue sample M and the lower surface of the absorption filter 41 is denoted by reference symbol d, and an interval between an upper surface of the absorption filter 41 and the light receiving surface 31A of the light receiving unit 31 is denoted by reference symbol c. The interval f, the interval e and the interval c are 0 μm. That is, the light emitting surface 30A of the light source unit 30 and the lower surface of the band-pass filter 40 are brought into close contact with each other, and the upper surface of the band-pass filter 40 and the lower surface of the tissue sample M are also brought into close contact with each other. The upper surface of the absorption filter 41 and the light receiving surface 31A of the light receiving unit 31 are also brought into close contact with each other.

When the light emitting surface 30A of the light source unit 30 and the lower surface of the band-pass filter 40 are brought into close contact with each other, then the light emitted from the light emitting surface 30A of the light source unit 30 is made incident on the band-pass filter 40 without spreading. In accordance with this configuration in which the light emitting surface 30A of the light source unit 30 and the lower surface of the band-pass filter 40 are brought into close contact with each other, wraparound of a signal to an adjacent pixel, such as crosstalk, is reduced particularly in a transmission mode to be described later. Accordingly, this configuration is preferable since it is easy to obtain a two-dimensionally quantified image with high quantitativeness. Note that, when the light source unit 30 applies parallel light, even if the light emitting surface 30A of the light source unit 30 and the lower surface of the band-pass filter 40 are spaced apart from each other, the light emitted from the light emitting surface 30A is made incident on the band-pass filter 40 without spreading. Therefore, when the light source unit 30 applies parallel light, the interval denoted by reference symbol f described above can take a value of 0 μm or more.

In contrast, though the interval d between the upper surface of the tissue sample M and the lower surface of the absorption filter 41, which is shown in FIG. 4 and FIG. 5, is not particularly limited, the interval d usually ranges from 0 to 600 μm, preferably ranges from 0 to 50 μm, more preferably ranges from 0 to 20 μm. That is, the upper surface of the tissue sample M and the lower surface of the absorption filter 41 are disposed so as to be brought into close contact with each other, or to be spaced apart from each other at the predetermined interval d. When the upper surface of the tissue sample M and the lower surface of the absorption filter 41 are in close contact with each other, the tissue sample M is sandwiched between the light source unit 30 and the light receiving unit 31, and resolution of the obtained two-dimensional image is increased. Note that, when high resolution of the two-dimensional image is not required, the interval d between the upper surface of the tissue sample M and the lower surface of the absorption filter 41 can be set within the range of, for example, 600 μm or less as described above. In general, as the resolution of the two-dimensional image is increased as the interval d takes a numerical value closer to 0 μm.

In order to dispose the tissue sample M between the upper surface of the band-pass filter 40 and the lower surface of the absorption filter 41, the light receiving unit 31 is made vertically movable in a Z-direction. Such vertical movement of the light receiving unit 31 is performed by operating a positioning unit 50 for the light receiving unit in accordance with an instruction from the control unit 100. The light source unit 30 is fixed to a fixed stage (not shown), and the light receiving unit 31 is fixed to a movable stage (not shown).

As described above, the positioning unit 50 for the light receiving unit is operated in accordance with the instruction from the control unit 100, and the light receiving unit 31 moves vertically. In this way, as shown in FIG. 5, the interval d between the upper surface of the tissue sample M and the lower surface of the absorption filter 41 can be adjusted in a state in which the tissue sample M is mounted on the upper surface of the band-pass filter 40. Note that laser ranging or the like is used for confirmation of the numerical value of the interval d.

The first embodiment adopts a configuration capable of vertically moving the light receiving unit 31 side in the Z-direction by using the positioning unit 50 for the light receiving unit. However, in place of this or in addition to this, it may be made possible to vertically move the light source unit 30 side in the Z-direction by operating a positioning unit (not shown) for the light source unit in accordance with an instruction from the control unit 100.

In the tissue sample analysis device 1, first, as shown in FIG. 1, a user mounts the tissue sample M on a base (scanning stage) 55, and then the base 55 is put from the opening portion 22 of the housing 21 into the housing 21. Next, the stage drive unit 34 is configured to be capable of moving the base 55 between the light source unit 30 and the light receiving unit 31 in accordance with the instruction from the control unit 100, and capable of moving the tissue sample M from the base 55 to the upper surface of the band-pass filter 40 in accordance therewith.

Note that, when the tissue sample M is measured by the tissue sample analysis device 1, the tissue sample M is usually held on a preparation or the like, which is made of glass or the like. For example, in fluorescent immunohistochemical staining, if there is used a substance that does not completely solidify as an mounting medium when the tissue sample is fixed to the preparation, then it is not preferable to place the preparation upside down since cover glass is temporarily attached. As described above, when the tissue sample M is held on the preparation or the like, which is made of glass or the like, the measurement is performed in a state in which the tissue sample M is not completely fixed. Accordingly, the light source unit 30 is disposed on a lower side that is a slide glass side of the preparation, and the light receiving unit 31 is disposed on an upper side thereof. Therefore, FIG. 2 to FIG. 5 show the tissue sample analysis device 1, in which the light source unit 30 is disposed on the lower side, and the light receiving unit 31 is disposed on the upper side.

However, in the tissue sample analysis device 1 according to the first embodiment, the light source unit 30 and the light receiving unit 31 may be configured to be movable so that the state in which the light source unit 30 is disposed on the lower side and the light receiving unit 31 is disposed on the upper side can be reversed upside down. For example, if the preparation using the tissue sample M can be reversed upside down, then the light source unit 30 and the light receiving unit 31 are rotated while holding the tissue sample M therebetween, whereby the state in which the light source unit 30 is disposed on the lower side and the light receiving unit 31 is disposed on the upper side may be changed to the state in which the light source unit 30 is disposed on the upper side and the light receiving unit 31 is disposed on the lower side. An example of the preparation that is reversible upside down includes a preparation that is free from apprehension of falling off of the cover glass or the tissue sample M by the fact that the mounting medium completely solidifies.

Note that, when the preparation using the tissue sample M is not reversible upside down, the tissue sample analysis device is used in such a state in which the light source unit 30 and the light receiving unit 31 are not reversed upside down. As such a tissue sample analysis device in which the light source unit 30 and the light receiving unit 31 are not reversed upside down, for example, there are used: the tissue sample analysis device 1 shown in FIG. 2 to FIG. 5; and a tissue sample analysis device in which the light source unit 30 and the light receiving unit 31 are fixed though the light source unit 30 and the light receiving unit 31 are reversible upside down. An example of the preparation that is not reversible upside down includes a preparation from which it is apprehended that the cover glass may fall off and the tissue sample M may consequently fall off, the cover glass being temporarily attached by the mounting medium since the mounting medium does not solidify. For example, as a preparation when the tissue sample M is stained fluorescent immunohistochemically or the like, a preparation that is not reversible upside down is used.

Moreover, in the present invention, when measurement targets include the cover glass and the tissue sample, which are not likely to move, fall off, and so on by the fact that the mounting medium completely solidifies, the light source unit 30 may be disposed on the upper side and the light receiving unit 31 may be disposed on the lower side. Accordingly, as another embodiment (not shown), a tissue sample analysis device can be used, in which the light source unit 30 is disposed on the upper side, and the light receiving unit 31 is disposed on the lower side. As the tissue sample analysis device in which the light source unit 30 is disposed on the upper side and the light receiving unit 31 is disposed on the lower side, for example, a tissue sample analysis device can be used, in which such a state in which the light source unit 30 is disposed on the upper side and the light receiving unit 31 is disposed on the lower side is fixed. Moreover, as the tissue sample analysis device in which the light source unit 30 is disposed on the upper side and the light receiving unit 31 is disposed on the lower side, for example, a tissue sample analysis device can be used, in which the light source unit 30 and the light receiving unit 31 are rotated while holding the tissue sample M therebetween, whereby the state in which the light source unit 30 is disposed on the upper side and the light receiving unit 31 is disposed on the lower side can be changed to the state in which the light source unit 30 is disposed on the lower side and the light receiving unit 31 is disposed on the upper side.

<Function>

Next, a description will be made of an example of a function in a case of using the above-mentioned tissue sample analysis device 1, using the fluorescent substance as the test reagent, obtaining the two-dimensional distribution of the photometric information AS of the tissue sample M, and performing the quantification and the two-dimensional imaging for the tissue sample M.

[Measurement Using Blank Tissue Sample M without being Added with Fluorescent Substance]

First, photometric information AS ($AS_B$) is acquired in advance for such a blank tissue sample M without being added with the fluorescent substance. In the photometric information AS, the photometric information AS on the blank tissue sample M without being added with the fluorescent substance is also referred to as $AS_B$ in particular. The photometric information $AS_B$ is information composed of a numerical sequence in which coordinate information in the light receiving unit 31 is added to such photometric values RS ($RS_B$) of the blank tissue sample M without being added with the fluorescent substance.

The photometric information AS is acquired in a similar way to a procedure of "Measurement Using Tissue sample M Added with Fluorescent substance", which will be described later, except that the fluorescent substance is not added to the tissue sample M. For example, as shown in FIG. 2, the photometric information AS of the blank tissue sample M without being added with the fluorescent substance is acquired in advance by sandwiching the tissue sample M between the band-pass filter 40 and the absorption filter 41 in a state in which the band-pass filter 40 is disposed on the surface of the light emitting surface 30A of the light source unit 30 and the absorption filter 41 is disposed on the surface of the light receiving surface 31A of the light receiving unit 31.

Moreover, the photometric information $AS_B$ of the blank tissue sample M without being added with the fluorescent substance is processed in the data computing unit 14, whereby two-dimensional distribution information (distribution information $OD_B$) of the photometric information $AS_B$ is created in advance. The distribution information $OD_B$ is information composed of a numerical matrix in which the photometric values $RS_B$ are arranged based on the coordinate information in the light receiving unit 31, which is added to the photometric information $AS_B$. As shown in FIG. 2, the obtained distribution information $OD_B$ is stored in advance in the storage unit 15 and the image composition unit 13.

[Measurement Using Tissue Sample M Added with Fluorescent Substance]

Next, the user of the tissue sample analysis device 1 prepares the tissue sample M added with the fluorescent substance. For example, the tissue sample M is immunohistochemically stained by the fluorescent substance.

As shown in FIG. 1, the user mounts the tissue sample M, which is added with the fluorescent substance, on the base 55, and thereafter, as shown in FIG. 2, puts the base 55 from the opening portion 22 of the housing 21 into the housing 21. In accordance with an instruction from the control unit 100, the stage drive unit 34 moves the base 55 to the light source unit 30 side, and moves the tissue sample M from the base 55 to the upper surface of the band-pass filter 40.

Then, for example, the tissue sample M added with the fluorescent substance is brought into close contact with the band-pass filter 40 and the absorption filter 41 between the light emitting surface 30A, on which the LEDs of the light source unit 30 are arranged, and the light receiving surface 31A of the light receiving unit 31. Note that the tissue sample M and the absorption filter 41 may be spaced apart from each other. Wavelengths of light generated by the respective LEDs of the light source unit 30 stay within the range from ultraviolet rays to visible light.

Fluorescence excitation light in the light of each LED of the light source unit 30 transmits through the band-pass filter 40, and reaches the tissue sample M added with the fluorescent substance. The fluorescent substance in the tissue sample M is excited by the fluorescence excitation light of each LED of the light source unit 30, and emits fluorescence. The fluorescence emitted from the fluorescent substance in the entire region of the tissue sample M transmits through the absorption filter 41, and reaches the light receiving surface 31A on which the CMOS image sensor elements as a large number of the photoelectric conversion elements of the light receiving unit 31 are arranged. Other light such as leakage light of the excitation light is blocked by the absorption filter 41.

The light receiving unit 31 measures intensity of the fluorescence emitted by the fluorescent substance for each of the large number of CMOS image sensor elements, which compose the light receiving surface 31A, and on the entire CMOS image sensor elements present on the light receiving surface 31A, whereby the photometric values RS are obtained. The photometric value RS is obtained by the number of CMOS image sensor elements. Note that, since the light receiving surface 31A of the light receiving unit 31 includes the tissue sample M and is formed larger than the tissue sample M, the photometric values RS are obtained for the entire light receiving unit 31 including the entire region of the tissue sample M. Moreover, the photometric values RS are added with the coordinate information of the CMOS image sensor elements on the light receiving surface 31A of the light receiving unit 31, and become the photometric information AS.

The photometric information AS is sent to the control unit 100 after the photometric values RS included therein are amplified by the light receiving signal amplification unit 33.

The CMOS image sensor elements which compose the light receiving unit 31 are arranged, for example, in a state of being partitioned in a matrix grid pattern at a pitch of several microns. One cell of the CMOS image sensor elements corresponds to one pixel. Therefore, each of such intensities (photometric values RS) of the fluorescence of the fluorescent substance distributed in the entire region of the tissue sample M has resolution of several microns. Moreover, the photometric information AS obtained by adding the coordinate information of the CMOS image sensor elements on the light receiving surface 31A of the light receiving unit 31 to the photometric values RS is formed for the entire CMOS image sensor elements on the light receiving surface 31A of the light receiving unit 31. Accordingly, the photometric information AS is formed so as to cover the entire region of the tissue sample M smaller in area than the light receiving surface 31A. Therefore, in accordance with the tissue sample analysis device 1, the intensities (photometric values RS) of the fluorescence of the fluorescent substance distributed over the entire region of the tissue sample M can be measured over the entire region of the tissue sample M with a resolution of several microns simultaneously in a short time, for example, in several minutes.

Moreover, the data computing unit 14 computes and creates the distribution information OD of the photometric information AS for composing the two-dimensional image from the photometric information AS formed by the tissue sample analysis unit 20. For example, in order to display and make it easy to see, on the display unit 11, the distribution information OD of the photometric information AS for composing the two-dimensional image, as for color display of the distribution information OD, the data computing unit 14 can adjust magnitude of each of the intensities of colors thereof, can select types of display colors, and so on.

The control unit 100 sends the distribution information OD of the photometric information AS for composing the adjusted image to the image composition unit 13. For example, the image composition unit 13 superimposes the distribution information OD of the tissue sample M, which is added with the fluorescent substance, on the distribution information $OD_B$ of the blank tissue sample M without being added with the fluorescent substance, thereby composing the colorized two-dimensionally imaged data GD of the tissue sample M.

Here, the two-dimensionally imaged data GD means general-purpose image data created based on a certain rule in order to store the distribution information OD. As the two-dimensionally imaged data GD, for example, a two-dimensional image in which the distribution information OD is color-coded based on such a certain rule is used in order to visualize data. The color coding is realized, for example, in such a manner that intensity values of the photometric values RS included in the photometric information AS are classified by a histogram or the like, and that pixels corresponding to coordinates of the coordinate information owned by the photometric information AS are color-painted in response to classes to which the intensity values of the photometric values RB belong. Note that this color coding may be performed by color painting with colors of different hues. Moreover, in order to record gradation values of the photometric values RS in the distribution information OD as they are, a 16-bit numerical matrix, in which the photometric values RS are constructed based on the coordinates of the photometric information AS, may be expressed by using an image format that is a 16-bit monochrome image format. An image format at this time may be an existing general-purpose format or an intrinsic and unique format. The two-dimensionally imaged data GD is sent from the image composition unit 13 to the control unit 100.

Figure 7:
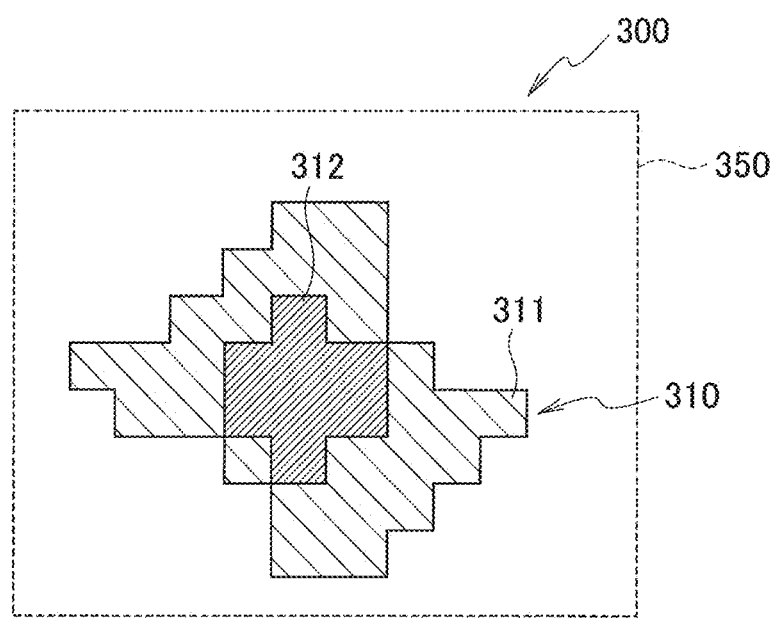
FIG. 7 is a view showing an example of a two-dimensionally quantified image obtained by adding a fluorescent substance to the tissue sample M shown in FIG. 6.

The control unit 100 displays the two-dimensionally quantified image on the display unit 11 based on the two-dimensionally imaged data GD of the tissue sample M. Specific examples of the two-dimensionally quantified images are shown in FIG. 1 and FIG. 7. The colorized image of the analysis example EX shown in FIG. 1 can be displayed, for example, in a state in which it is made easy to see the distribution (intensity distribution) of the intensities (photometric value RS) of the fluorescence of the fluorescent substance distributed in the entire region of the tissue sample M.

Figure 6:
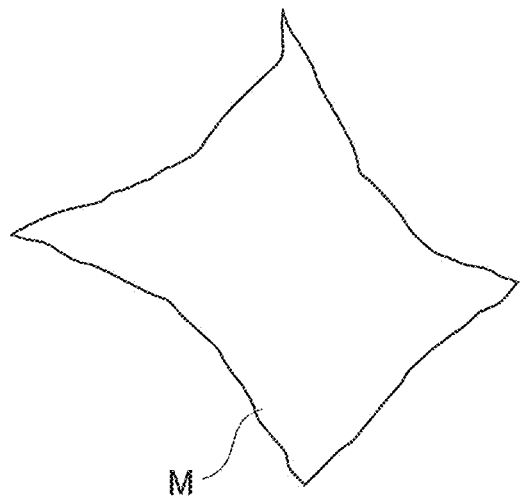
FIG. 6 is a view showing an example of the tissue sample M.

Moreover, FIG. 7 is an example of the two-dimensionally quantified image obtained by adding the fluorescent substance to the tissue sample M shown in FIG. 6. In a two-dimensionally quantified image 300 shown in FIG. 7, a mosaic two-dimensionally quantified image body 310 composed of an aggregate of the square pixels of the CMOS image sensor elements is displayed in a rectangular two-dimensionally quantified image region 350. The two-dimensionally quantified image body 310 has a shape similar to that of such a rhombic tissue sample M shown in FIG. 6 and displays the photometric values RS at the respective areas of the tissue sample M in response to the intensity values. Specifically, in the two-dimensionally quantified image body 310, a peripheral portion of a rhombic shape, which is similar to an outer shape of the tissue sample M, is a portion 311 with low photometric values RS, and a central portion thereof is a portion 312 with high photometric values RS. A level of each of the photometric values RS corresponds to an amount of the fluorescent substance in the tissue sample M, and accordingly, in accordance with the two-dimensionally quantified image body 310 shown in FIG. 7, it is understood that the amount of the fluorescent substance in the tissue sample M is larger in the central portion than in the peripheral portion.

As described above, in accordance with the tissue sample analysis device 1, the light source unit 30 and the light receiving unit 31 are used, whereby a distribution state of tones of the fluorescent substance distributed in the tissue sample M can be measured in a short time at resolution of several microns over the whole of the tissue sample M.

<Effect>

The tissue sample analysis device 1 according to the first embodiment of the present invention is not a so large-scale system as heretofore, but can be downsized, and in addition, is low in price.

In accordance with the tissue sample analysis device 1, the measurement can be performed only by disposing the tissue sample M between the light source unit 30 and the light receiving unit 31, and accordingly, an analysis operation by an operator is easy, operability is satisfactory, an analysis time is short, and resolution is also sufficient.

Moreover, in accordance with the tissue sample analysis device 1 having such a configuration, the tissue sample M can be disposed between the light source unit 30 and the light receiving unit 31, the distribution state of the tones and the like of the fluorescent substance distributed in the entire region of the tissue sample M can be acquired as the photometric information AS at one time, and the two-dimensional imaging can be performed based on the photometric information AS. Therefore, in accordance with the tissue sample analysis device 1 having such a configuration, the analysis time for quantifying the tissue sample M and performing the two-dimensional imaging is short.

In accordance with the tissue sample analysis device 1, since the analysis time is short as described above, the operation of analyzing the chemical substance localized in the tissue sample M in the living body and quantifying the chemical substance in the minute range of the tissue sample M can be completed before the tissue sample M deteriorates. Therefore, in accordance with the tissue sample analysis device 1, a result of the quantitative analysis can be acquired earlier in a more minute range of the tissue sample M.

In accordance with the tissue sample analysis device 1, the size of the light source unit 30 and the light receiving unit 31 is set as appropriate, whereby, regardless of the size of the tissue sample M ranging from that of a small animal to a large one of human, the distribution state of the tones of the fluorescent substance distributed in the tissue sample M can be acquired, can be formed into a two-dimensional image, and can be analyzed in a short time.

Moreover, in accordance with the tissue sample analysis device 1, the light emission wavelengths of the respective LEDs of the light source unit 30 and the fluorescent substance for use in the immunohistochemical staining are selected and combined with each other, whereby plural types of the biological substances distributed in the same tissue sample (tissue sample) M can be analyzed quantitatively at the same time.

In the tissue sample analysis device 1, the measurement can be performed only by disposing the tissue sample M between the light source unit 30 and the light receiving unit 31, and accordingly, the distribution of the fluorescent substance in the whole of the tissue sample M can be acquired as the photometric information AS at one time in a short time. As described above, the distribution of the fluorescent substance can be acquired as the photometric information AS at one time in a short time, and accordingly, in accordance with the tissue sample analysis device 1, such a deterioration of the tissue sample M due to aging can be prevented, and variations in technique of the operator of the experiment are less likely to occur.

Moreover, in accordance with the tissue sample analysis device 1, when the tissue sample M is sandwiched between the light source unit 30 and the light receiving unit 31, the tissue sample M can be measured in a photometric manner while being flattened even if flatness of the tissue sample M is poor. Therefore, in accordance with the tissue sample analysis device 1 having such a configuration, the reproducibility of the quantitative analysis (quantitative value) of the tissue sample M can be enhanced.

Note that, when a thickness of the tissue sample M is large, the chemical substance in the tissue sample M is often localized. Therefore, if a conventional microscope-type device is used when the thickness of the tissue sample M is large, then in many cases, accurate numerical values of the tissue sample M cannot be measured since such a microscope is not focused.

On the other hand, when the tissue sample analysis device 1 is used to sandwich the tissue sample M between the light source unit 30 and the light receiving unit 31, the distance between the light source unit 30 and the light receiving unit 31 can be made constant. Therefore, in accordance with the tissue sample analysis device 1 having such a configuration, even when the thickness of the tissue sample M is large, the tissue sample M can enhance the accuracy of the quantitative analysis (quantitative value) of the tissue sample M itself.

In the tissue sample analysis device 1, the light source unit 30 is fixed to the fixed stage. Therefore, in accordance with the tissue sample analysis device 1, the measuring work is simple, and variations in measured values by the operator can be suppressed.

In the tissue sample analysis device 1, when the size of the light source unit 30 and the light receiving unit 31 is larger than the size of the tissue sample M, the light source unit 30 and the light receiving unit 31 can cover the entire region of the tissue sample M.

Therefore, when the size of the light source unit 30 and light receiving unit 31 of the tissue sample analysis device 1 is larger than the size of the tissue sample M, the photometric information AS necessary to compose the two-dimensional image of the entire area of the tissue sample M can be acquired at one time regardless of the area size of the tissue sample M. Therefore, in accordance with the tissue sample analysis device 1 having such a configuration, it is not necessary to perform a scanning operation, the photometry can be performed in a short time, and the reproducibility of the quantitative analysis is enhanced. Moreover, in accordance with the tissue sample analysis device 1 having such a configuration, the photometric information AS necessary to compose the two-dimensional image of the entire region of the tissue sample M can be acquired at one time before the tissue sample M deteriorates, and a analysis of the tissue sample M having a large size can be easily carried out. Therefore, it is also possible to construct a three-dimensional image (3D image).

When the tissue sample M is sandwiched between the light source unit 30 and the light receiving unit 31, even if the tissue sample M is wavelike and the flatness of the tissue sample M is poor, the tissue sample M can be sandwiched and fixed between the light source unit 30 and the light receiving unit 31. Therefore, in accordance with the tissue sample analysis device 1 having such a configuration, the tissue sample M is fixed by using the light source unit 30 and the light receiving unit 31. Hence, in accordance with the tissue sample analysis device 1 having such a configuration, an amount of the fluorescence can be accumulated to obtain the distribution of the tones of the fluorescence over the entire region of the tissue sample M without using a lens system, whereby the tissue sample M can be analyzed quantitatively without being affected by the poor flatness of the tissue sample M.

Moreover, when the tissue sample M is sandwiched between the light source unit 30 and the light receiving unit 31, such quantitative analysis is not affected by the thickness of the tissue sample M (at which the chemical substance is localized). Therefore, in accordance with the tissue sample analysis device 1 having such a configuration, the quantitative analysis of the tissue sample M can be carried out without including errors. Moreover, in accordance with the tissue sample analysis device 1 having such a configuration, the tissue sample M can be analyzed quantitatively by using the light source unit 30 and the light receiving unit 31, without using a lens, by accumulating the amount of light, and without including errors.

Moreover, in accordance with the tissue sample analysis device 1 having such a configuration, the light source unit 30 and the light receiving unit 31 are used, and a lens that causes aberration is not used, and accordingly, the tissue sample M can be subjected to accurate quantitative analysis.

Second Embodiment

A description will be made of a second embodiment of the present invention with reference to FIG. 8 and FIG. 9.

Figure 8:
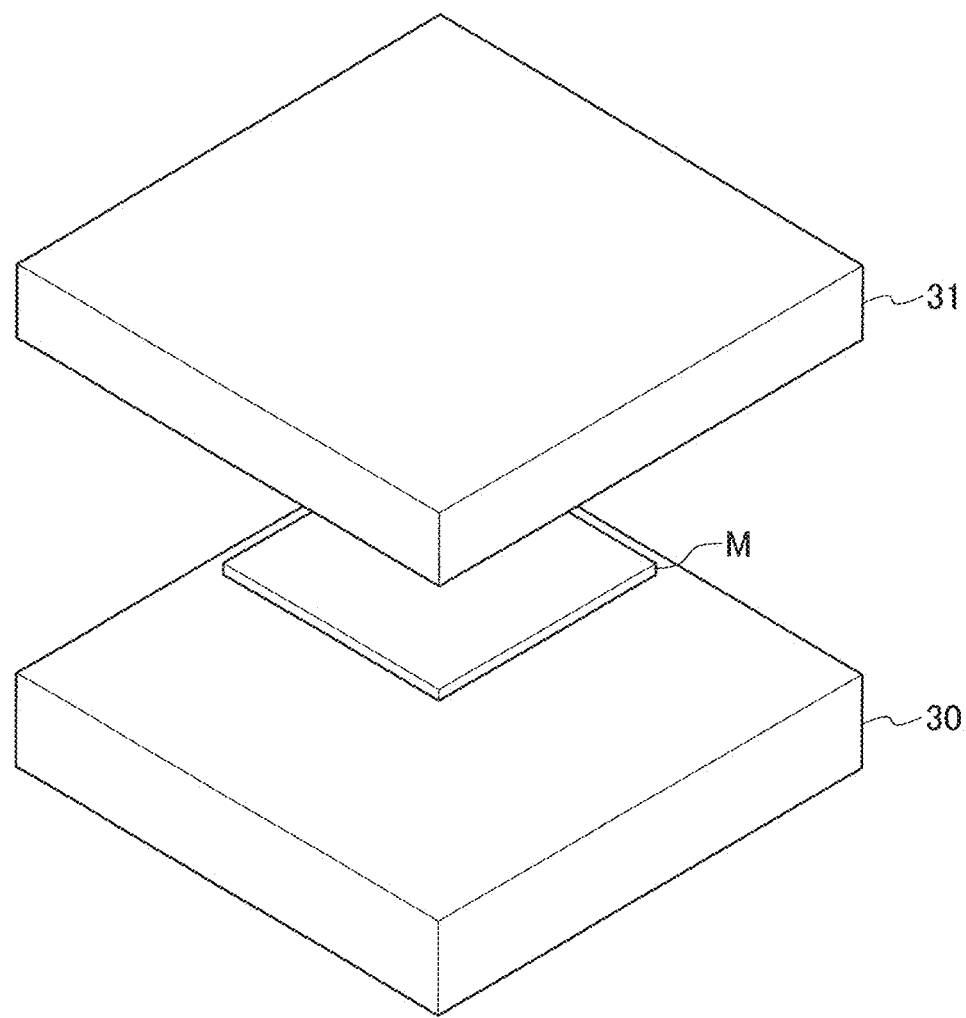
FIG. 8 is a perspective view showing a tissue sample analysis device according to a second embodiment of the present invention.
Figure 9:
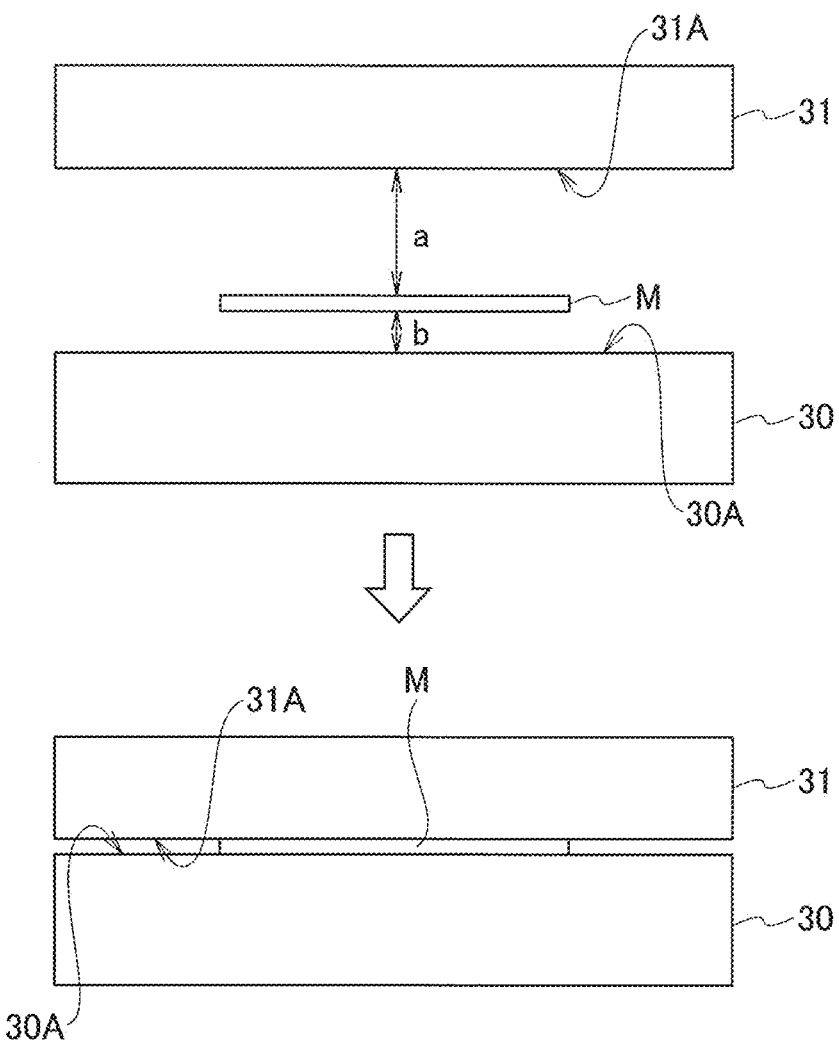
FIG. 9 is a front view showing the tissue sample analysis device according to the second embodiment of the present invention.

In the second embodiment of the present invention, which is shown in FIG. 8 and FIG. 9, the same reference numerals are assigned to the same constituents as those of the first embodiment shown in FIG. 1 and FIG. 2, and a description thereof will be omitted. The second embodiment of the present invention, which is shown in FIG. 8 and FIG. 9, differs from the first embodiment of the present invention in the following points, but is similar thereto in other aspects.

A photometric system that composes the first embodiment of the present invention, which is shown in FIG. 4 and FIG. 5, is a photometric system for measuring the tissue sample M, which is added with the fluorescent substance, in a photometric manner and in a so-called fluorescence mode by using the tissue sample M.

In contrast, a photometric system that composes the second embodiment of the present invention, which is shown in FIG. 8 and FIG. 9, is a photometric system for measuring such a tissue sample M, which is not added with the fluorescent substance, in a photometric manner and in a so-called transmission mode of photometric measurement by transmitting light through the tissue sample M by using the tissue sample M. When such a tissue sample M as lipid, which is unsuitable for the immunohistochemical staining, is subjected to the photometric measurement, a general histochemical stain or the like is used as a test reagent.

The photometric system of the transmission mode, which composes the second embodiment shown in FIG. 8 and FIG. 9, is a photometric system formed by removing the band-pass filter 40 and the absorption filter 41 from the photometric system of the fluorescence mode, which composes the first embodiment shown in FIG. 4 and FIG. 5. The photometric system of the transmission mode, which is shown in FIG. 8 and FIG. 9, does not include the band-pass filter 40 and the absorption filter 41, and accordingly, can reduce cost by reducing the number of parts in the case of being used for determining a lesion or the like by using a bright field observation image such as general histochemical staining or the like. Accordingly, the photometric system of the transmission mode is preferable.

Note that, unlike the configuration shown in FIG. 8 and FIG. 9, the photometric system of the transmission mode can also adopt a configuration of including at least one of the band-pass filter 40 and the absorption filter 41. For example, the band-pass filter 40 can be disposed between the light source unit 30 and the tissue sample M as in the photometric system of the fluorescence mode, which composes the first embodiment shown in FIGS. 4 and 5. When the band-pass filter 40 is used, it becomes possible to transmit only a light component in a wavelength region, which corresponds to an absorption wavelength of a stained portion of the tissue sample M stained by the histochemical stain, out of the illumination light applied from the light source unit 30, and it becomes possible to apply the transmitted light component to the tissue sample M. Therefore, when the band-pass filter 40 is disposed as described above in the photometric system of the transmission mode, and the tissue sample M stained by the histochemical stain is measured in a photometric manner, then absorbance of the stained portion stained by the histochemical stain can be measured with accuracy. Moreover, if the band-pass filter 40 allows transmission of only such a light component in the wavelength region in which the stain such as the histochemical stain added to the tissue sample M is largely absorbed, out of the illumination light applied from the light source unit 30, then the absorbance of the stained portion stained by the histochemical stain can be measured with higher accuracy when the tissue sample M stained by the histochemical stain is measured in a photometric manner.

Moreover, for example, the absorption filter 41 can be disposed between the light receiving unit 31 and the tissue sample M as in the photometric system of the fluorescence mode, which composes the first embodiment shown in FIGS. 4 and 5. When the absorption filter 41 is used, it becomes possible to transmit only a light component in a wavelength region, which corresponds to an absorption wavelength of a stained portion of the tissue sample M stained by the histochemical stain, out of the light radiated by the tissue sample M stained by the histochemical stain, and it becomes possible to apply the transmitted light component to the light receiving unit 31. Therefore, when the absorption filter 41 is disposed as described above in the photometric system of the transmission mode, and the tissue sample M stained by the histochemical stain is measured in a photometric manner, then the absorbance of the stained portion stained by the histochemical stain can be measured with accuracy. Moreover, if the absorption filter 41 transmits only such a light component in the wavelength region in which the stain such as the histochemical stain added to the tissue sample M is largely absorbed, out of the light radiated from the tissue sample M stained by the histochemical stain, then the absorbance of the stained portion stained by the histochemical stain can be measured with higher accuracy when the tissue sample M stained by the histochemical stain is measured in a photometric manner.

Moreover, for example, the absorption filter 41 can be disposed between the light receiving unit 31 and the tissue sample M as in the photometric system of the fluorescence mode, which composes the first embodiment shown in FIGS. 4 and 5. When the absorption filter 41 is used, it becomes possible to transmit only the light component in the wavelength region, which corresponds to the absorption wavelength of the stained portion of the tissue sample M stained by the histochemical stain, and it becomes possible to apply the transmitted light component to the light receiving unit 31. Therefore, when the absorption filter 41 is disposed as described above in the photometric system of the transmission mode, and the tissue sample M stained by the histochemical stain is measured in a photometric manner, then the absorbance of the stained portion stained by the histochemical stain can be measured with accuracy.

In the photometric system of the transmission mode, which is shown in FIG. 9, an interval between the light emitting surface 30A of the light source unit 30 and the lower surface of the tissue sample M is denoted by reference symbol b, and the interval between the upper surface of the tissue sample M and the light receiving surface 31A of the light receiving unit 31 is denoted by reference symbol a. An interval b is 0 μm, and the tissue sample M is brought into close contact with the upper surface 30A of the light source unit 30. In contrast, an interval a ranges from 0 to 50 μm for example, and preferably ranges from 0 to 20 μm. That is, the upper surface of the tissue sample M and the light receiving surface 31A of the light receiving unit 31 are disposed so as to be brought into close contact with each other, or to be spaced apart from each other at the predetermined interval a.

As described above, in the photometric system of the transmission mode, which composes the second embodiment, as shown in FIG. 9, the tissue sample M is disposed so as to be tightly sandwiched between the upper surface 30A of the light source unit 30 and the light receiving surface 31A of the light receiving unit 31. The wavelengths of light generated by the respective LEDs of the light source unit 30 stay within the range from the ultraviolet rays to the visible light.

<Function>

A function of the second embodiment differs from the function of the tissue sample analysis device 1 according to the first embodiment in that the photometric system is the photometric system for the transmission mode, and other functions are similar therebetween. Therefore, among the functions of the second embodiment, a description of the same functions as those of the tissue sample analysis device 1 according to the first embodiment will be omitted.

In the second embodiment, since the band-pass filter 40 as described in the first embodiment is not provided between the light source unit 30 and the tissue sample M, the light of each LED of the light source unit 30 reaches the tissue sample M as it is. In the light that has reached the tissue sample M, a density of the target substance in the stained tissue sample M is measured as a transmittance value (photometric value RS) in a photometric manner by the light receiving unit 31. Moreover, in the light receiving unit 31, as in the first embodiment, the coordinate information in the light receiving unit 31 is added to the photometric value RS, and the photometric information AS is created. The light receiving unit 31 can measure the entire tissue sample M in a short time at the resolution of several microns.

Moreover, in the second embodiment, it is also possible to simultaneously analyze a plurality of biological substances in the same tissue sample M by combination of the wavelengths of the respective LEDs of the light source unit 30 and types of the stain. For example, when plural types of the wavelengths of the LEDs of the light source unit 30 are prepared, and plural types of stains corresponding to any of these plural types of the wavelengths are used, it becomes possible to simultaneously analyze the plurality of biological substances in the same tissue sample M.

Next, a description will be made of a tissue sample analysis system by using the drawings.

[Tissue Sample Analysis System]

Third Embodiment

Figure 10:
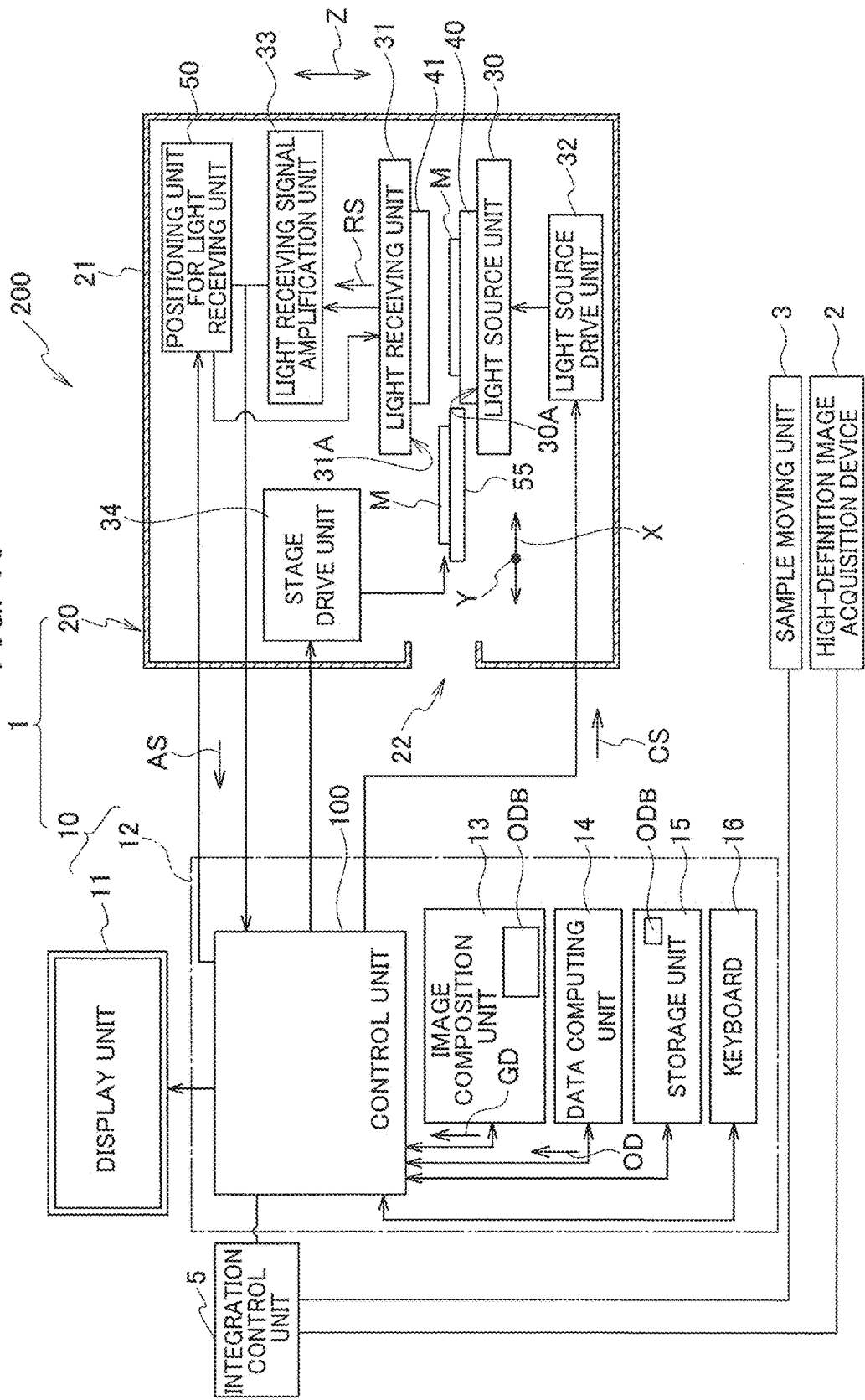
FIG. 10 is a block diagram showing a configuration example of a tissue sample analysis system according to a third embodiment of the present invention.

FIG. 10 is a block diagram showing a configuration example of a tissue sample analysis system according to a third embodiment of the present invention.

As shown in FIG. 10, a tissue sample analysis system 200 includes the tissue sample analysis device 1 according to the first embodiment, a high-definition image acquisition device 2, and an integration control unit 5. The integration control unit 5 is electrically connected to the control unit 100 of the tissue sample analysis device 1 and the high-definition image acquisition device 2. Moreover, the tissue sample analysis system 200 includes a sample moving unit 3 electrically connected to the integration control unit 5.

The high-definition image acquisition device 2 is a device that acquires a high-definition image of the tissue sample. As the high-definition image acquisition device 2, for example, a microscope is used. The microscope usually has a lens and an image sensor. Therefore, the high-definition image acquired by the high-definition image acquisition device 2 is usually an image obtained by the microscope having the lens and the image sensor.

Here, as the tissue sample, a tissue sample of a living body, which is the same as the tissue sample for use in the tissue sample analysis device 1, is used. Moreover, the term "high-definition image" means an image having resolution equal to or higher than the resolution of the photoelectric conversion elements such as the CMOS image sensor elements which compose the light receiving unit 31 of the tissue sample analysis device 1.

Note that the tissue sample analysis device 1 does not have a lens for enlargement. Therefore, the two-dimensionally quantified image created by the tissue sample analysis device 1 is an image created based on the photometric values RS obtained not via optical enlarging means such as a lens but via only the photoelectric conversion elements such as the image sensors of the light receiving unit 31. Therefore, the resolution of the two-dimensionally quantified image crated by the tissue sample analysis device 1 is lower than that of the high-definition image. That is, the high-definition image acquired by the high-definition image acquisition device 2 is an image with higher definition than that of the two-dimensionally quantified image created by the tissue sample analysis device 1. The two-dimensionally quantified image and the high-definition image will be described in detail later. In general, however, the two-dimensionally quantified image has an advantage in being excellent in quantitativeness, and the high-definition image has an advantage in being high in the resolution. For example, the tissue sample analysis system 200 exhibits the advantage of the two-dimensionally quantified image in being excellent in quantitativeness, and in addition, is used so as to compensate for the low resolution of the two-dimensionally quantified image by exhibiting the advantage of the high-definition image.

The integration control unit 5 has a function to associate the two-dimensionally quantified image created by the tissue sample analysis device 1 and the high-definition image acquired by the high-definition image acquisition device with each other. The integration control unit 5 acquires the two-dimensionally quantified image from the control unit 100 of the tissue sample analysis device 1, and in addition, acquires the high-definition image from the high-definition image acquisition device 2, and associates the two-dimensionally quantified image and the high-definition image with each other. When the two-dimensionally quantified image and the high-definition image are associated with each other, for example, a two-dimensional image composite is formed. Here, the term "two-dimensional image composite" means an image composite in which the two-dimensionally quantified image and the high-definition image coexist in association with each other.

The sample moving unit 3 has a function to control to move the tissue sample M so that the tissue sample M can be analyzed by the tissue sample analysis device 1 and that an image can be acquired by the high-definition image acquisition device 2. Specifically, the sample moving unit 3 performs control to move the tissue sample M onto the base 55 of the tissue sample analysis device 1 and onto an imaging base (not shown) of the high-definition image acquisition device 2.

Figure 11:
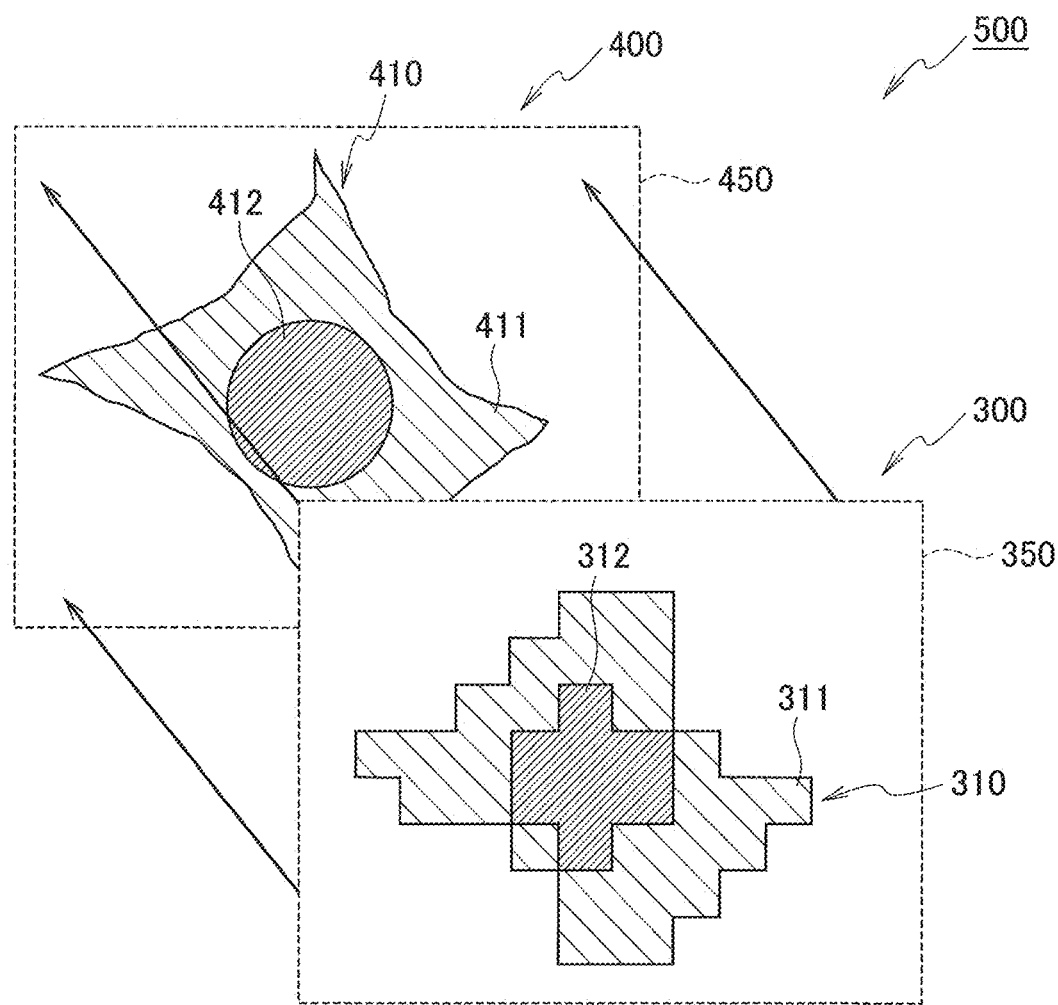
FIG. 11 is a view showing an example of a configuration of a two-dimensional image composite, which is composed of the two-dimensionally quantified image and a high-definition image, which are obtained by adding the fluorescent substance to the tissue sample M shown in FIG. 6.
Figure 12:
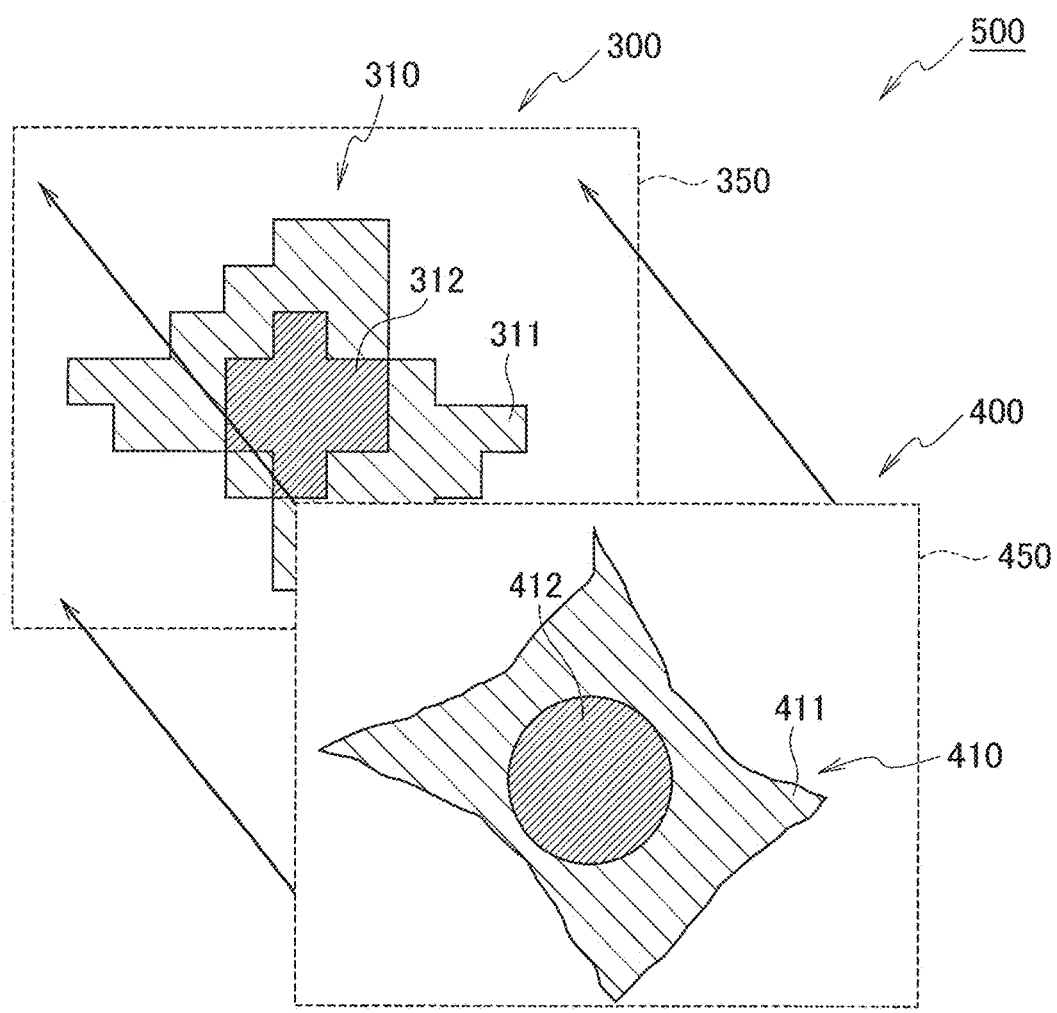
FIG. 12 is a view showing an example of the configuration of the two-dimensional image composite, which is composed of the two-dimensionally quantified image and the high-definition image, which are obtained by adding the fluorescent substance to the tissue sample M shown in FIG. 6.

Referring to the drawings, a description will be made of the two-dimensionally quantified image created by the tissue sample analysis device 1, the high-definition image acquired by the high-definition image acquisition device 2, and the two-dimensional image composite composed by associating the two-dimensionally quantified image and the high-definition image with each other. FIG. 11 and FIG. 12 are views showing an example of a configuration of a two-dimensional image composite 500, which is composed of the two-dimensionally quantified image 300 and a high-definition image 400, which are obtained by adding the fluorescent substance to the tissue sample M shown in FIG. 6. In the two-dimensional image composite 500 shown in FIG. 11 and FIG. 12, only the image on a near side in each of FIG. 11 and FIG. 12 is displayed on an actual screen of the display unit 11. That is, in the two-dimensional image composite 500 shown in FIG. 11, only the two-dimensionally quantified image 300 is displayed on the actual screen of the display unit 11, and the high-definition image 400 is not displayed thereon. Moreover, in the two-dimensional image composite 500 shown in FIG. 12, only the high-definition image 400 is displayed on the actual screen of the display unit 11, and the two-dimensionally quantified image 300 is not displayed thereon.

The two-dimensionally quantified image 300 is the same as the two-dimensionally quantified image 300 shown in FIG. 7. That is, in the two-dimensionally quantified image 300, the mosaic two-dimensionally quantified image body 310 composed of the aggregate of the square pixels of the CMOS image sensor elements is displayed in the rectangular two-dimensionally quantified image region 350. The two-dimensionally quantified image body 310 has a shape similar to that of such a rhombic tissue sample M shown in FIG. 6 and displays the photometric values RS at the respective areas of the tissue sample M in response to the intensity values. Specifically, in the two-dimensionally quantified image body 310, a peripheral portion of a rhombic shape, which is similar to an outer shape of the tissue sample M, is a portion 311 with low photometric values RS, and a central portion thereof is a portion 312 with high photometric values RS. The level of each of the photometric values RS corresponds to the amount of the fluorescent substance in the tissue sample M, and accordingly, in accordance with the two-dimensionally quantified image body 310 shown in FIG. 11 and FIG. 12, it is understood that the amount of the fluorescent substance in the tissue sample M is larger in the central portion than in the peripheral portion.

In the high-definition image 400, the rhombic high-definition image body 410 is displayed in the rectangular high-definition image region 450. The high-definition image body 410 is a high-definition image corresponding to the two-dimensionally quantified image body 310 of the two-dimensionally quantified image 300. A portion 411 in the high-definition image body 410 is a portion corresponding to the portion 311 with the low photometric values RS in the two-dimensionally quantified image 300. A portion 412 in the high-definition image body 410 is a portion corresponding to the portion 312 with the high photometric values RS in the two-dimensionally quantified image 300. The resolution of the high-definition image 400 is higher than that of the two-dimensionally quantified image 300, and accordingly, accuracy of an outline thereof is improved.

Here, a description will be made of advantages and disadvantages of the two-dimensionally quantified image 300 and the high-definition image 400. The two-dimensionally quantified image 300 is an image formed by processing information such as the photometric values RS, and in addition, does not use enlarging means such as a lens, and accordingly, the two-dimensionally quantified image 300 is free from aberration. Therefore, the two-dimensionally quantified image 300 has such an advantage in being excellent in quantitativeness in comparison with the high-definition image 400 to be described later. Meanwhile, since a limit of the resolution depends on the size of the photoelectric conversion elements such as the image sensors, the two-dimensionally quantified image 300 has a disadvantage in being low in resolution in comparison with the high-definition image 400 to be described later.

In contrast, since the enlarging means such as a lens is used for the high-definition image 400, the high-definition image 400 has an advantage in being high in resolution in comparison with the two-dimensionally quantified image 300. Meanwhile, the high-definition image 400 is not such an image formed by processing the information such as the photometric values RS, and the high-definition image 400 is formed via the enlarging means such as a lens, and accordingly, aberration occurs therein. Therefore, the high-definition image 400 has such a disadvantage in being low in quantitativeness in comparison with the two-dimensionally quantified image 300.

As described above, each of the two-dimensionally quantified image 300 and the high-definition image 400 has the advantage and the disadvantage. Each of the two-dimensional image composites 500 shown in FIG. 11 and FIG. 12 associates the two-dimensionally quantified image 300 and the high-definition image 400 with each other, thus making it possible to easily exhibit the individual advantages of the two-dimensionally quantified image 300 and the high-definition image 400.

The two-dimensional image composite 500 in a state shown in FIG. 11 is formed so as to make it possible to easily exhibit the advantage of the two-dimensionally quantified image 300. For example, in accordance with the two-dimensional image composite 500 in the state shown in FIG. 11, the advantage in being excellent in quantitativeness is exhibited.

In contrast, the two-dimensional image composite 500 in a state shown in FIG. 12 is formed so as to make it possible to easily exhibit the advantage of the high-definition image 400. For example, in accordance with the two-dimensional image composite 500 in the state shown in FIG. 12, the advantage in being high in resolution is exhibited.

In the two-dimensional image composite 500, the two-dimensionally quantified image 300 and the high-definition image 400 are associated with each other, and on the screen of the display unit 11, it is made possible to display at least one of the two-dimensionally quantified image 300 and the high-definition image 400, and to switch such display between the quantified image 300 and the high-definition image 400. For example, setting is made to enable other image than the currently displayed image, which is the two-dimensionally quantified image 300 or the high-definition image 400, to be displayed if the currently displayed image is clicked. Note that the way of setting is not particularly limited.

<Function>

The function of the tissue sample analysis system 200 is a sum obtained by adding a function to analyze the same tissue sample M, which is moved by the sample moving unit 3, by the tissue sample analysis device 1, and to acquire an image by the known high-definition image acquisition device 2, and a function to associate the two-dimensionally quantified image 300, which is created by the tissue sample analysis device 1, and the high-definition image 400, which is acquired by the high-definition image acquisition device 2, with each other to the function of the above-described tissue sample analysis device 1 and the function of the known high-definition image acquisition device 2.

The two-dimensionally quantified image 300 created by the tissue sample analysis device 1 and the high-definition image 400 acquired by the high-definition image acquisition device 2 are associated with each other by the integration control unit 5. A way of such association is not particularly limited.

When the two-dimensionally quantified image 300 and the high-definition image 400 are associated with each other, as described above, the individual advantages of the two-dimensionally quantified image 300 and the high-definition image 400 can be easily exhibited.

Note that, in the tissue sample analysis system 200, the tissue sample analysis device according to the second embodiment may be used in place of the tissue sample analysis device 1 according to the first embodiment.

Fourth Embodiment

Figure 13:
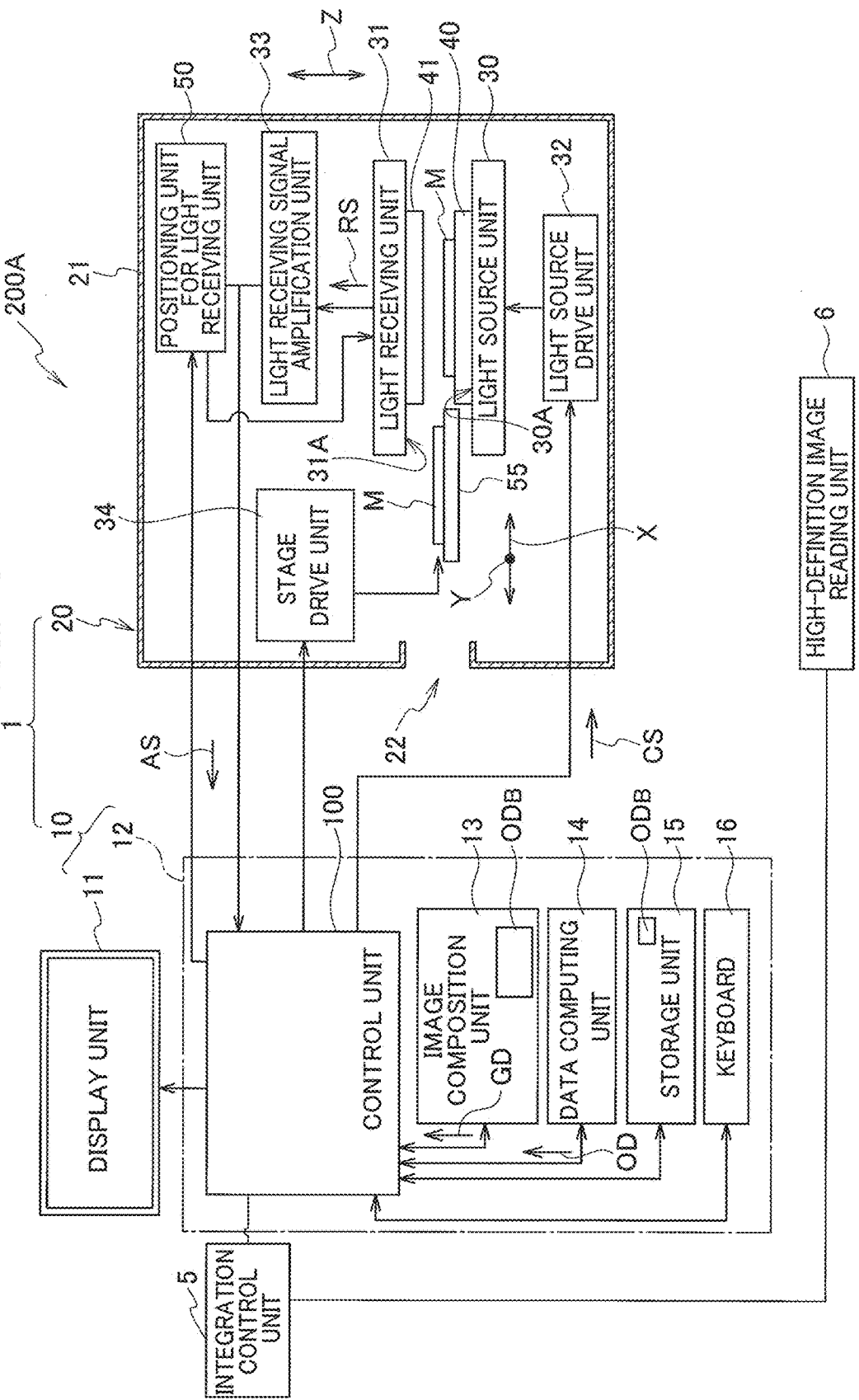
FIG. 13 is a block diagram showing a configuration example of a tissue sample analysis system according to a fourth embodiment of the present invention.

FIG. 13 is a block diagram showing a configuration example of a tissue sample analysis system according to a fourth embodiment of the present invention.

As shown in FIG. 13, a tissue sample analysis system 200A includes the tissue sample analysis device 1 according to the first embodiment, a high-definition image reading unit 6, and an integration control unit 5. The integration control unit 5 is electrically connected to the control unit 100 of the tissue sample analysis device 1 and the high-definition image reading unit 6.

The tissue sample analysis system 200A according to the fourth embodiment, which is shown in FIG. 13, is the same as the tissue sample analysis system 200 according to the third embodiment, which is shown in FIG. 11, except that the high-definition image reading unit 6 is provided in place of the high-definition image acquisition device 2, and that the sample moving unit 3 is not provided. Therefore, the same reference numerals are assigned to the same constituents in the tissue sample analysis system 200A according to the fourth embodiment and the tissue sample analysis system 200 according to the third embodiment, and a description of the configuration and the function will be omitted or simplified.

The high-definition image reading unit 6 has a function to read a high-definition image of the tissue sample, which is acquired by a high-definition image acquisition device (not shown) or the like. As the high-definition image reading unit 6, a known image reading device can be used. Note that the high-definition image of the tissue sample, which is acquired by the high-definition image acquisition device or the like, is defined to be a high-definition image acquired from the same tissue sample M as the tissue sample M analyzed by the tissue sample analysis device 1 according to the first embodiment.

<Function>

A function of the tissue sample analysis system 200A is the same as that of the tissue sample analysis system 200 except that there is no function to move the tissue sample M by the sample moving unit 3 while there is a function to read the high-definition image from another high-definition image acquisition device in place of acquiring the high-definition image by the high-definition image acquisition device 2. Therefore, a description of the function of the tissue sample analysis system 200A will be omitted.

Note that, in the tissue sample analysis system 200A, the tissue sample analysis device according to the second embodiment may be used in place of the tissue sample analysis device 1 according to the first embodiment.

(Effect of Tissue Sample Analysis Device)

The above-mentioned tissue sample analysis device 1 according to above-mentioned respective embodiments of the present invention can quantify and image the tissue sample M at the cellular level, and can achieve the downsizing and cost reduction of the device, simplification of the analysis work, acceleration of the analysis work, and enhancement of the resolution of the image of the entire region of the tissue sample M.

The tissue sample analysis device 1 can instantaneously acquire the distribution information and the like of the chemical substance, which is unevenly distributed and contained in the tissue sample M as a biological specimen, for example, in a manner of capturing contents of a document on a desk by a scanner.

Since a time required for the analysis is short in the tissue sample analysis device 1, the tissue sample analysis device 1 can not only analyze the large tissue sample M with ease but becomes capable of analyzing a large number of continuous tissue samples, and can construct a three-dimensional image.

In the conventional device, for example, it takes about 30 minutes to analyze the mouse brain slice and about 20 hours to analyze the human brain slice; however, in the embodiments of the present invention, one slice can be analyzed in several minutes regardless of the size of the tissue sample M. Resolution of one measurement region (pixel in image data) can be increased from several tens of microns to a several micron level, and fine and quantified image data can be obtained. Then, according to the purpose of the research, the measured values of the respective measurement regions of the tissue sample M can be easily extracted and statistically processed.

As described above, the tissue sample analysis device 1 according to each of the embodiments of the present invention is a tissue sample analysis device for analyzing the photometric information of the tissue sample M of the living body, which includes: the light source unit 30 that applies light onto the tissue sample M; and the flat light receiving unit 31 that is disposed opposite to the light source unit 30 and receives the light from the tissue sample M in a state in which the tissue sample M is sandwiched between the light source unit 30 and the light receiving unit 31 itself or in a state in which the tissue sample M is disposed between the light source unit 30 and the light receiving unit 31 itself without being sandwiched therebetween.

In this way, the tissue sample M is sandwiched between the light source unit 30 and the light receiving unit 31 or is disposed between the light source unit 30 and the light receiving unit 31 without being sandwiched therebetween, and accordingly, the distribution of the fluorescent substance of the entire tissue sample can be acquired at one time in a short time. As described above, the time deterioration of the tissue sample can be prevented, and variations in technique of the operator of the experiment do not occur. Moreover, the tissue sample M is disposed between the light source unit 30 and the light receiving unit 31 by being sandwiched therebetween, and accordingly, the tissue sample M can be measured in a photometric manner while being flattened even if the flatness of the tissue sample M is poor.

From these facts, the tissue sample analysis device can be downsized, the analysis work for the tissue sample M can be accelerated, and in addition, it becomes possible to quantify and image the chemical substance unevenly distributed in the tissue sample M.

In the tissue sample analysis device 1, the fluorescent substance is added to the tissue sample M, the band-pass filter that passes therethrough the light having a wavelength that allows the fluorescent substance to emit light is disposed between the light source unit 30 and the tissue sample M, and the absorption filter that transmits therethrough the fluorescence from the fluorescent substance of the tissue sample M is disposed between the tissue sample M and the light receiving unit 31.

In this way, the band-pass filter gives the tissue sample M only the light, which has the wavelength that fluoresces the fluorescent substance added to the tissue sample M, the fluorescence emitted by the fluorescent substance of the tissue sample M transmits through the absorption filter, and the leakage light of the other excitation light and the like are blocked by the absorption filter, and accordingly, the light receiving unit 31 can be surely allowed to receive only the fluorescence. Therefore, it becomes possible to quantify and image the chemical substance unevenly distributed in the tissue sample M.

Among the tissue sample analysis devices 1, the tissue sample analysis device 1 according to the second embodiment, which includes the photometric system in the transmission mode, is used while adding a stain as the reagent to the tissue sample M. In this way, for example, the tissue sample M such as lipid, which is unsuitable for the immunohistochemical staining, is dyed with such a general histochemical stain or the like, and accordingly, in a photometric manner, the light receiving unit 31 can measure the distribution of the concentration of the target substance in the tissue sample M as a distribution of the transmittance.

In the tissue sample analysis device 1, the light source unit 30 is composed by arranging the plurality of light emitting diodes in two dimensions, and the light receiving unit 31 is composed by two-dimensionally arranging the solid-state image sensors. In this way, it is only necessary to arrange, as the light source unit 30, the plurality of light emitting diodes in two dimensions, and only necessary to two-dimensionally arrange the solid-state image sensors as the light receiving unit 31, and there is no need to use a large microscope or photomultiplier or both of them. Accordingly, the tissue sample analysis device 1 can be downsized to a large extent, and cost thereof can be reduced to a large extent.

Although the present invention has been described with reference to the embodiments, each of the embodiments is merely an example, and the scope of the invention described in the claims can be variously changed within the scope without departing from the spirit of the invention.

For example, the light source unit 30 uses the plurality of LEDs (light emitting diodes); however, the present invention is not limited to this, and as another example of the light source unit 30, EL (electroluminescence) may be composed in a flat plate shape. Even in this case, it is only necessary to compose, as the light source unit 30, the EL in a flat plate shape, and only necessary to two-dimensionally arrange the solid-state image sensors as the light receiving unit 31, and there is no need to use such a large microscope or photomultiplier or both of them. Accordingly, the tissue sample analysis device 1 can be downsized to a large extent, and cost thereof can be reduced to a large extent.

In FIG. 4, a polarizing filter may be disposed between the upper surface 30A of the light emitting unit 30 and the lower surface of the band-pass filter 40.

Note that, in the tissue sample analysis device 1, a scanning stage may be attached to one or more of the light source unit 30, the light receiving unit 31 and the base 55, the scanning stage being capable of moving vertically, horizontally and so on for thereto. When such a scanning stage is attached, a measurement range can be widened.

Furthermore, in the tissue sample analysis device 1, if the light source unit 30 and the light receiving unit 31 are large, then it is apprehended that the tissue sample analysis unit 20 may increase in size and may increase in cost. In this case, with regard to either one or more of the light source unit 30 and the light receiving unit 31, the area thereof is reduced, and in addition, the either one or more are fixed to the movable stages, whereby an observation range may be ensured or enlarged.

Moreover, the tissue sample analysis device 1 may be provided with a protection mechanism that prevents damage due to contact between the light source unit 30 or the light receiving unit 31 and the tissue sample M or the preparation containing the tissue sample M.

As such a protector, for example, a spacer, a restraint or the like is used. Here, the spacer is sandwiched between the light source unit 30 or the light receiving unit 31 and the tissue sample M or the preparation containing the tissue sample M, thereby preventing direct contact and breakage thereof. Moreover, the restraint is means for limiting movement of one or more members of the light source unit 30, the light receiving unit 31, the tissue sample M, and the preparation containing the tissue sample M. In the present invention, when the above-described protector is used, distances between one or more members of the light source unit 30, the light receiving unit 31, the band-pass filter 40, the absorption filter 41, the tissue sample M, and the preparation containing the tissue sample M, for example, the interval c, the interval d, the interval e, the interval f and the like can be arbitrarily set in place of the above-described numerical ranges.

(Effect of Tissue Sample Analysis System)

In accordance with the tissue sample analysis system of the present invention, in addition to the effect of the tissue sample analysis device according to the present invention, it is possible to analyze the chemical substance in the tissue sample M by the two-dimensional image composite in which the quantified image with excellent quantitativeness and the high-definition image with high resolution are linked and associated with each other by the coordinates.

The entire contents of Japanese Patent Application No. 2015-138702 (filed on: Jul. 10, 2015) is incorporated herein by reference.

REFERENCE SIGNS LIST

1 TISSUE SAMPLE ANALYSIS DEVICE
2 HIGH-DEFINITION IMAGE ACQUISITION DEVICE
3 SAMPLE MOVING UNIT
5 INTEGRATION CONTROL UNIT
6 HIGH-DEFINITION IMAGE READING UNIT
10 CONTROL DEVICE
11 DISPLAY UNIT
12 CONTROL BODY UNIT
13 IMAGE COMPOSITION UNIT
14 DATA COMPUTING UNIT
15 STORAGE UNIT
20 TISSUE SAMPLE ANALYSIS UNIT
21 HOUSING
30 LIGHT SOURCE UNIT
31 LIGHT RECEIVING UNIT
40 BAND-PASS FILTER
41 ABSORPTION FILTER
M TISSUE SAMPLE

100 CONTROL UNIT
200 TISSUE SAMPLE ANALYSIS SYSTEM
300 TWO-DIMENSIONALLY QUANTIFIED IMAGE
310 TWO-DIMENSIONALLY QUANTIFIED IMAGE BODY
311 PORTION WITH LOW PHOTOMETRIC VALUE RS
312 PORTION WITH HIGH PHOTOMETRIC VALUE RS
350 TWO-DIMENSIONALLY QUANTIFIED IMAGE REGION
400 HIGH-DEFINITION IMAGE
410 HIGH-DEFINITION IMAGE BODY
411 PORTION WITH SMALL AMOUNT OF FLUORESCENCE
412 PORTION WITH LARGE AMOUNT OF FLUORESCENCE
500 TWO-DIMENSIONAL IMAGE COMPOSITE

The invention claimed is:

1. A lens-less tissue sample analysis device not having a lens for optical enlargement that quantitatively analyzes a tissue sample of a macroscopic specimen of a living body by using photometric information AS obtained by applying light to the tissue sample while maintaining a tissue structure of the tissue sample, whereby quantitatively analyzes an amount of the chemical substance localized in the tissue sample having a size of a minute range of a cellular level by measuring the amount of the chemical substance in the entire region of thickness direction of the tissue sample, and obtains a quantified image in which a distribution of the chemical substance is arranged two-dimensionally, the tissue sample analysis device comprising:
  a light source unit that a band-pass filter is disposed between the light source unit and the tissue sample, and applies the light to the tissue sample;
  a flat light receiving unit that is disposed opposite to the light source unit, is partitioned in a matrix grid pattern at a pitch of several microns, and in a state in which the tissue sample is disposed between the light source unit and the light receiving unit itself, receives light transmitted through the tissue sample or light radiated from the tissue sample;
  a tissue sample analysis unit that acquires the photometric information AS from the tissue sample not via a lens for optical enlargement; and
  a control device that creates information based on the photometric information AS acquired by the tissue sample analysis unit;
  wherein the photometric information AS is information by adding coordinate information in the light receiving unit to photometric values RS, the photometric values RS being information obtained in such a manner that the light receiving unit converts light into an electrical signal, the light being illumination light applied from the light source unit and transmitted through the tissue sample or the light being radiated from the tissue sample, and obtained amount of the light are accumulated over the thickness direction of in the tissue sample;
  the control device includes a display unit and a control body unit;
  the control body unit includes:
    a control unit that output a control signal,
    a data computing unit that creates a distribution information OD of the photometric information AS based on the photometric information AS obtained from the tissue sample analysis unit, and
    an image composition unit that compose a imaged data GD which is image data for displaying an image on the display unit based on the distribution information OD;
  the control unit that displays the quantified image on the display unit based on the imaged data GD: and
  the data computing unit quantitatively analyzes the amount of the chemical substance by performing the computational processing based on the photometric values RS in the photometric information AS and a coordinate information in the light receiving unit, and measuring the amount of the chemical substance and a distribution thereof in the entire region of thickness direction and planar direction in the tissue sample.

2. The tissue sample analysis device according to claim 1, wherein the light applied to the tissue sample by the light source unit is parallel light.

3. The tissue sample analysis device according to claim 1, wherein the light source unit is flat.

4. The tissue sample analysis device according to claim 1, wherein the tissue sample is a tissue sample added with a test reagent.

5. The tissue sample analysis device according to claim 1, wherein the test reagent is a fluorescent substance,
  a band-pass filter that allows transmission of excitation light exciting the fluorescent substance added to the tissue sample is disposed between the light source unit and the tissue sample, and
  an absorption filter that allows transmission of fluorescence radiated from the fluorescent substance added to the tissue sample is disposed between the tissue sample and the light receiving unit.

6. The tissue sample analysis device according to claim 1, wherein the test reagent is stain.

7. The tissue sample analysis device according to claim 1, wherein a band-pass filter that allows transmission of only a light component in a wavelength region in which the stain added to the tissue sample is largely absorbed is disposed between the light source unit and the tissue sample.

8. The tissue sample analysis device according to claim 1, wherein an absorption filter that allows the transmission of only the light component in the wavelength region in which the stain added to the tissue sample is largely absorbed is disposed between the tissue sample and the light receiving unit.

9. The tissue sample analysis device according to claim 1, wherein the light receiving unit is composed by two-dimensionally arranging solid-state image sensors.

10. The tissue sample analysis device according to claim 1, wherein the light source unit is composed by arranging a plurality of light emitting diodes in two dimensions.

11. The tissue sample analysis device according to claim 1,
  wherein the light source unit is composed of electroluminescence in a flat plate shape, and
  the light receiving unit is composed by two-dimensionally arranging solid-state image sensors.

12. The tissue sample analysis device according to claim 1, wherein a protection mechanism that prevents damage due to contact between the light source unit or the light receiving unit and the tissue sample or the preparation containing the tissue sample is provided.

13. A tissue sample analysis system comprising:
  the tissue sample analysis device according to claim 1;
  a high-definition image acquisition device that acquires a high-definition image of the tissue sample; and an integration control unit that associates the quantified image created by the tissue sample analysis device and the high-definition image acquired by the high-definition image acquisition device with each other.

14. A tissue sample analysis system comprising:
the tissue sample analysis device according to claim 1;
a high-definition image reading unit that reads a high-definition image of the tissue sample; and
an integration control unit that associates the quantified image created by the tissue sample analysis device and the high-definition image read by the high-definition image reading unit with each other.

* * * * *